United States Patent [19]
Harrison et al.

[11] Patent Number: 5,824,678
[45] Date of Patent: Oct. 20, 1998

[54] MORPHOLINE DERIVATIVES AND THEIR USE AS THERAPEUTIC AGENTS

[75] Inventors: Timothy Harrison, Great Dunmow; Andrew Pate Owens, Rushden; Christopher John Swain, Duxford, all of Great Britain

[73] Assignee: Merck Sharp & Dohme Ltd., Hoddesdon, England

[21] Appl. No.: 793,186

[22] PCT Filed: Aug. 7, 1995

[86] PCT No.: PCT/GB95/01868

§ 371 Date: Feb. 13, 1997

§ 102(e) Date: Feb. 13, 1997

[87] PCT Pub. No.: WO96/05181

PCT Pub. Date: Feb. 22, 1996

[30] Foreign Application Priority Data

Aug. 15, 1994 [GB] United Kingdom .............. 9416427
May 11, 1995 [GB] United Kingdom .............. 9509605

[51] Int. Cl.$^6$ ............. A61K 31/533; C07D 265/32; C07D 413/06
[52] U.S. Cl. ............ 514/237.8; 544/87; 544/111; 544/521; 544/139; 544/141; 544/143; 544/162
[58] Field of Search ................. 544/162; 514/237.8

[56] References Cited

U.S. PATENT DOCUMENTS 5,612,337  3/1997  Baker et al. ............... 514/236.2

FOREIGN PATENT DOCUMENTS 0 528 495  2/1993  European Pat. Off. .
0 577 394  1/1994  European Pat. Off. .
WO 95/16679  6/1995  WIPO .

Primary Examiner—Robert W. Ramsuer
Attorney, Agent, or Firm—J. Eric Thies; David L. Rose

[57] ABSTRACT

The present invention relates to compounds of formula (I)

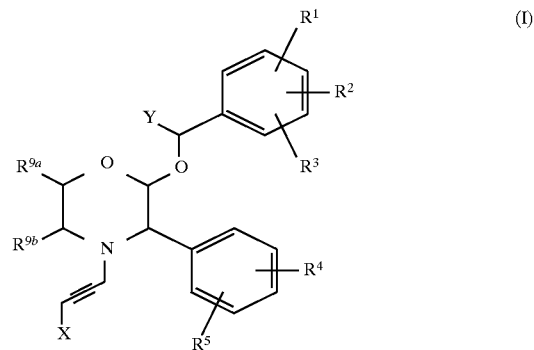

wherein X is —$NR^6R^7$ or C— or N-linked imidazolyl; Y is hydrogen or $C_{1-4}$alkyl optionally substituted by hydroxy; $R^1$, $R^2$, $R^3$, $R^4$ and $R^5$ are selected from a variety of suitable aromatic substituents; $R^6$ is hydrogen, $C_{1-6}$alkyl, $C_{3-7}$cycloalkyl, $C_{3-7}$cycloalkyl$C_{1-4}$alkyl, phenyl, or $C_{2-4}$alkyl substituted by $C_{1-4}$alkoxy or hydroxy; $R^7$ is hydrogen, $C_{1-6}$alkyl, $C_{3-7}$cycloalkyl, $C_{3-7}$cycloalkyl $C_{1-4}$alkyl, phenyl, or $C_{2-4}$alkyl substituted by one or two of $C_{1-4}$alkoxy, hydroxy or a 4, 5 or 6 membered heteroaliphatic ring containing one or two heteroatoms selected from N, O and S; or $NR^6R^7$ is a saturated or partially saturated heterocyclic ring of 4 to 7 ring atoms, optionally containing one of O, S, $NR^8$, S(O) or $S(O)_2$ and optionally substituted by one or two of hydroxy$_{1-4}$alkyl, $C_{1-4}$alkoxy $C_{1-4}$alkyl, oxo, $COR^a$ or $CO_2R^a$; or $NR^6R^7$ forms a non-aromatic azabicyclic ring system of 6 to 12 ring atoms; and $R^{9a}$ and $R^{9b}$ are each independently hydrogen or $C_{1-4}$alkyl, or $R^{9a}$ and $R^{9b}$ are joined so, together with the carbon atoms to which they are attached, there is formed a $C_{5-7}$ring; or a pharmaceutically acceptable salt thereof. The compounds are of particular use in the treatment or prevention of pain, inflammation, migraine, emesis and postherpetic neuralgia.

17 Claims, No Drawings

MORPHOLINE DERIVATIVES AND THEIR USE AS THERAPEUTIC AGENTS

This application is a 371 PCT/GB95/01868 filed Aug. 7, 1995.

This invention relates to a class of morpholine derivatives which are useful as tachykinin antagonists.

The tachykinins are a group of naturally occurring peptides found widely distributed throughout mammalian tissues, both within the central nervous system and in peripheral nervous and circulatory systems.

At present, there are three known mammalian tachykinins referred to as substance P, neurokinin A (NKA, substance K, neuromedin L) and neurokinin B (NKB, neuromedin K) (for review see J. E. Maggio, *Peptides* (1985) 6(suppl. 3), 237–242). The current nomenclature designates the three tachykinin receptors mediating the biological actions of substance P, NKA and NKB as the $NK_1$, $NK_2$ and $NK_3$ receptors, respectively.

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, proliferative vitreoretinopathy, irritable bowel syndrome and disorders of bladder function including cystitis and bladder detruser hyper-reflexia is reviewed in "Tachykinin Receptors and Tachykinin Receptor Antagonists", C. A. Maggi, R Patacchini, P. Rovero and A. Giachetti, *J. Auton. Pharmacol.* (1993) 13, 23–93.

For instance, substance P is believed inter alia to be involved in the neurotransmission of pain sensations [Otsuka et al, "Role of Substance P as a Sensory Transmitter in Spinal Cord and Sympathetic Ganglia" in 1982 Substance P in the Nervous System, *Ciba Foundation Symposium* 91, 13–34 (published by Pitman) and Otsuka and Yanagisawa, "Does Substance P Act as a Pain Transmitter?" *TIPS* (1987) 8, 506–510], specifically in the transmission of pain in migraine (B. E. B. Sandberg et al, *J. Med Chem*, (1982) 25, 1009) and in arthritis [Levine et al in *Science* (1984) 226, 547–549]. Tachykinins have also been implicated in gastrointestinal (GI) disorders and diseases of the GI tract such as inflammatory bowel disease [Mantyh et al in *Neuroscience* (1988) 25(3), 817–37 and D. Regoli in "Trends in Cluster Headache" Ed. Sicuteri et al Elsevier Scientific Publishers, Amsterdam (1987) page 85)] and emesis [F. D. Tattersall et al, *Eur. J. Pharmacol.*, (1993) 250, R5–R6]. It is also hypothesised that there is a neurogenic mechanism for arthritis in which substance P may play a role [Kidd et al "A Neurogenic Mechanism for Symmetrical Arthritis" in *The Lancet,* 11 Nov. 1989 and Grönblad et al, "Neuropeptides in Synovium of Patients with Rheumatoid Arthritis and Osteoarthritis" in *J. Rheumatol.* (1988) 15(12), 1807–10]. Therefore, substance P is believed to be involved in the inflammatory response in diseases such as rheumatoid arthritis and osteoarthritis, and fibrositis [O'Byrne et al, *Arthritis and Rheumatism* (1990) 33, 1023–8]. Other disease areas where tachykinin antagonists are believed to be useful are allergic conditions [Hamelet et al, *Can. J. Pharmacol. Physiol.* (1988) 66, 1361–7], immunoregulation [Lotz et al, *Science* (1988) 241, 1218–21 and Kimball et al, *J. Immunol.* (1988) 141(10), 3564–9] vasodilation, bronchospasm, reflex or neuronal control of the viscera [Mantyh et al, *Proc. Natl. Acad. Sci., USA* (1988) 85, 3235–9] and, possibly by arresting or slowing β-amyloid-mediated neurodegenerative changes [Yankner et al, *Science* (1990) 250, 279–82] in senile dementia of the Alzheimer type, Alzheimer's disease and Down's Syndrome.

Tachykinin antagonists may also be useful in the treatment of small cell carcinomas, in particular small cell lung cancer (SCLC) [Langdon et al, *Cancer Research* (1992) 52, 4554–7].

Substance P may also play a role in demyelinating diseases such as multiple sclerosis and amyotrophic lateral sclerosis [J. Luber-Narod et al, poster *C.I.N.P. XVIIIth Congress,* 28th Jun. 2nd Jul. 1992], and in disorders of bladder function such as bladder detrusor hyper-reflexia (*The Lancet,* 16th May 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophilic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosus (European patent specification no. 0 436 334), ophthalmic disease such as conjuctivitis, vernal conjunctivitis, and the like, and cutaneous diseases such as contact dermatitis, atopic dermatitis, urticaria, and other eczematoid dermatitis (European patent specification no. 0 394 989).

European patent specification no. 0 577 394 (published 5th Jan. 1994) discloses morpholine and thiomorpholine tachykinin receptor antagonists of the general formula

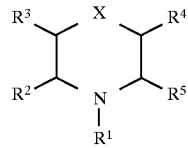

wherein $R^1$ is a large variety of substituents;
$R^2$ and $R^3$ are inter alia hydrogen;
$R^4$ is inter alia

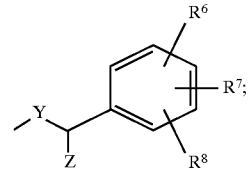

$R^5$ is inter alia optionally substituted phenyl;
$R^6$, $R^7$ and $R^8$ are a variety of substituents;
X is O, S, SO or $SO_2$;
Y is inter alia O; and
Z is hydrogen or $C_{1-4}$alkyl.

We have now found a further class of non-peptides which are potent antagonists of tachykinins, especially of substance P.

It is desirable that compounds may be administered orally and by injection. Certain compounds have now been discovered which act as potent non-peptide tachykinin antagonists and which, by virtue of their advantageous aqueous solubility, are particularly easily formulated for administration by both the oral and injection routes, for example in aqueous media.

The present invention provides compounds of the formula (I):

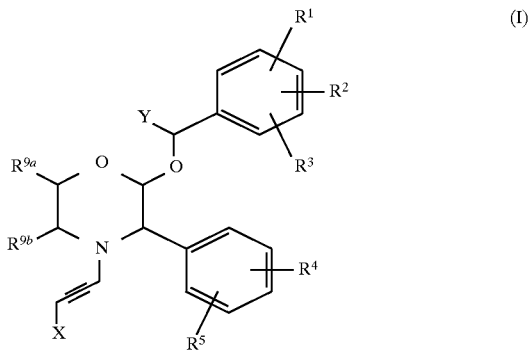

wherein
X is a group of the formula $NR^6R^7$ or a C— or N-linked imidazolyl ring;
Y is hydrogen or $C_{1-4}$alkyl optionally substituted by a hydroxy group;
$R^1$ is hydrogen, halogen, $C_{1-6}$alkyl, $C_{1-6}$alkoxy, $CF_3$, $NO_2$, CN, $SR^a$, $SOR^a$, $SO_2R^a$, $CO_2R$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ each independently represent hydrogen or $C_{1-4}$alkyl;
$R^2$ is hydrogen, halogen, $C_{1-6}$alkyl, $C_{1-6}$alkoxy substituted by $C_{1-4}$alkoxy or $CF_3$;
$R^3$ is hydrogen, halogen or $CF_3$;
$R^4$ is hydrogen, halogen, $C_{1-6}$alkyl, $C_{1-6}$alkoxy, hydroxy, $CF_3$, $NO_2$, CN, $SR^a$, $SOR^a$, $SO_2R^a$, $CO_2R^a$, $CONR^aR^b$, $C_{2-6}$alkenyl, $C_{2-6}$-alkynyl or $C_{1-4}$alkyl substituted by $C_{1-4}$alkoxy, wherein $R^a$ and $R^b$ are as previously defined;
$R^5$ is hydrogen, halogen, $C_{1-6}$alkyl, $C_{1-6}$alkoxy substituted by $C_{1-4}$alkoxy or $CF_3$;
$R^6$ is hydrogen, $C_{1-6}$alkyl, $C_{3-7}$cycloalkyl, $C_{3-7}$cycloalkyl$C_{1-4}$alkyl, phenyl, or $C_{2-4}$alkyl substituted by $C_{1-4}$alkoxy or hydroxy;
$R^7$ is hydrogen, $C_{1-6}$alkyl, $C_{3-7}$cycloalkyl, $C_{3-7}$cycloalkyl$C_{1-4}$alkyl, phenyl, or $C_{2-4}$alkyl substituted by one or two substituents selected from $C_{1-4}$alkoxy, hydroxy or a 4, 5 or 6 membered heteroaliphatic ring containing one or two heteroatoms selected from N, O and S;
or $R^6$ and $R^7$, together with the nitrogen atom to which they are attached, form a saturated or partially saturated heterocyclic ring of 4 to 7 ring atoms, which ring may optionally contain in the ring one oxygen or sulphur atom or a group selected from $NR^8$, S(O) or $S(O)_2$ and which ring may be optionally substituted by one or two groups selected from hydroxy$C_{1-4}$alkyl, $C_{1-4}$alkoxy$C_{1-4}$alkyl, oxo, $COR^a$ or $CO_2R^a$ where $R^a$ is as previously defined;
or $R^6$ and $R^7$ together with the nitrogen atom to which they are attached, form a non-aromatic azabicyclic ring system of 6 to 12 ring atoms;
$R^8$ is hydrogen, $C_{1-4}$alkyl, hydroxy$C_{1-4}$alkyl or $C_{1-4}$alkoxy$C_{1-4}$alkyl; and $R^{9a}$ and $R^{9b}$ are each independently hydrogen or $C_{1-4}$alkyl, or $R^{9a}$ and $R^{9b}$ are joined so, together with the carbon atoms to which they are attached, there is formed a $C_{5-7}$ ring; and pharmaceutically acceptable salts thereof.

A preferred class of compounds of formula (I) is that wherein $R^1$ is hydrogen, $C_{1-4}$alkyl, $C_{1-4}$alkoxy, halogen or $CF_3$.

Another preferred class of compounds of formula (I) is that wherein $R^2$ is hydrogen, $C_{1-4}$alkyl, $C_{1-4}$alkoxy, halogen or $CF_3$.

Also preferred is the class of compounds of formula (I) wherein $R^3$ is hydrogen, fluorine, chlorine or $CF_3$.

A particularly preferred class of compounds of formula (I) is that wherein $R^1$ is fluorine, chlorine or $CF_3$.

Another particularly preferred class of compounds of formula (I) is that wherein $R^2$ is hydrogen, fluorine, chlorine or $CF_3$.

Also particularly preferred is the class of compounds of formula (I) wherein $R^3$ is hydrogen, fluorine, chlorine or $CF_3$.

Preferably $R^1$ and $R^2$ are in the 3 and 5 positions of the phenyl ring.

More preferably $R^1$ is 3-fluoro or 3-$CF_3$.
More preferably $R^2$ is 5-fluoro or 5-$CF_3$.
More preferably $R^3$ is hydrogen.
Most preferably $R^1$ is 3-F or 3-$CF_3$, $R^2$ is 5-$CF_3$ and $R^3$ is hydrogen.

A further preferred class of compound of formula (I) is that wherein $R^4$ is hydrogen.

Another preferred class of compounds of formula (I) is that wherein $R^5$ is hydrogen, fluorine, chlorine or $CF_3$.

Preferably $R^4$ is hydrogen and $R^5$ is hydrogen or 4-fluoro.

Yet another preferred class of compounds of formula (I) is that wherein $R^6$ represents hydrogen, $C_{1-6}$alkyl or $C_{2-4}$alkyl substituted by $C_{1-6}$alkoxy.

A yet further preferred class of compounds of formula (I) is that wherein $R^7$ represents hydrogen, $C_{1-6}$alkyl or $C_{2-4}$alkyl substituted by $C_{1-6}$alkoxy.

Also preferred is the class of compounds of formula (I) wherein $R^6$ and $R^7$, together with the nitrogen atom to which they are attached, form a saturated heterocyclic ring of 4, 5 or 6 ring atoms which may optionally contain in the ring one oxygen atom or the group $NR^8$ (where $R^8$ is hydrogen or methyl) and which ring may be optionally substituted by hydroxy$C_{1-4}$alkyl, $C_{1-4}$alkoxy$C_{1-4}$alkyl, oxo, $COR^a$ or $CO_2R^a$.

In particular, the group $NR^6R^7$ preferably represents $NH_2$, $NHCH_3$, $N(CH_3)_2$, azetidinyl, morpholino, thiomorpholino, piperazino, piperidino or pyrrolidino.

Also preferred is the class of compounds of formula (I) wherein $R^{9a}$ and $R^{9b}$ are each independently hydrogen or methyl. Preferably $R^{9a}$ is hydrogen. Preferably $R^{9b}$ is hydrogen. Most preferably $R^{9a}$ and $R^{9b}$ are both hydrogen.

From the foregoing it will be appreciated that a particularly apt sub-group of compounds of this invention are those of the formula (Ia) and pharmaceutically acceptable salts thereof:

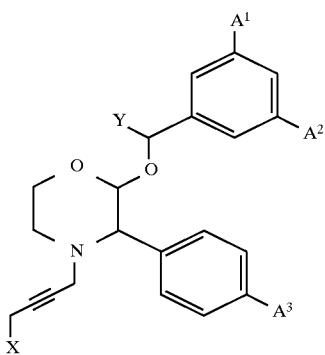

(Ia)

wherein
- $A^1$ is fluorine or $CF_3$;
- $A^2$ is fluorine or $CF_3$;
- $A^3$ is fluorine or hydrogen; and X and Y are as defined in relation to formula (I).

A preferred group X for compounds of formula (I) or (Ia) is the $NR^6R^7$ group where $R^6$ and $R^7$ each independently represent hydrogen, $C_{1-6}$alkyl or $C_{2-4}$alkyl substituted by $C_{1-6}$alkoxy, or $R^6$ and $R^7$, together with the nitrogen atom to which they are attached, form a saturated heterocyclic ring of 4, 5 or 6 atoms which may optionally contain in the ring one oxygen atom or the group $NR^8$, where $R^8$ is hydrogen or methyl.

A preferred group Y for compounds of the formulae (I) or (Ia) is the methyl or $CH_2OH$ group.

Where the group $NR^6R^7$ forms a saturated heterocylic ring of 4 to 7 ring atoms which may optionally contain in the ring one oxygen or sulphur atom or a group selected from $NR^8$, $S(O)$ or $S(O)_2$, suitable heterocyclic groups include azetidinyl, pyrrolidino, piperidino, homopiperidino, piperazino, N-methylpiperazino, morpholino and thiomorpholino.

Suitable substituents on the saturated heterocyclic ring include $CH_2OH$, $CH_2OCH_3$, oxo, CHO, $CO_2H$, $CO_2CH_3$, and $CO_2CH_2CH_3$.

When used herein the term "halogen" means fluorine, chlorine, bromine and iodine. The most apt halogen are fluorine and chlorine of which fluorine is preferred.

When used herein the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

The term "alkenyl" as a group or part of a group means that the group is straight or branched and contains at least one double bond. Examples of suitable alkenyl groups include vinyl and allyl.

The term "alkynyl" as a group or part of a group means that the group is straight or branched and contains at least one triple bond. An example of a suitable alkynyl group is propargyl.

Suitable cycloalkyl and cycloalkyl-alkyl groups include cyclopropyl, cyclobutyl, cyclopentyl, cyclohexyl, cyclopropylmethyl and cyclobutylmethyl.

Where the group $NR^6R^7$ represents a heteroaliphatic ring of 4 to 7 ring atoms and said ring is partially saturated, a particularly preferred group is 3-pyrroline.

Where the group $NR^6R^7$ represents a non-aromatic azabicyclic ring system, such a system may contain between 6 and 12, and preferably between 7 and 10, ring atoms.

Suitable rings include 5-azabicyclo[2.1.1]hexyl, 5-azabicyclo[2.2.1]heptyl, 6-azabicyclo[3.2.1]octyl, 2-azabicyclo[2.2.2]octyl, 6-azabicyclo[3.2.2]nonyl, 6-azabicyclo[3.3.1]nonyl, 6-azabicyclo[3.2.2]decyl, 7-azabicyclo[4.3.1]decyl, 7-azabicyclo[4.4.1]undecyl and 8-azabicyclo[5.4.1]dodecyl, especially 5-azabicyclo[2.2.1]heptyl and 6-azabicyclo[3.2.1]octyl.

Where $R^7$ represents a $C_{2-4}$alkyl group substituted by a 5 or 6 membered heteroaliphatic ring containing one or two heteroatoms selected from N, O and S, suitable rings include pyrrolidino, piperidino, piperazino, morpholino, or thiomorpholino. Particularly preferred are nitrogen containing heteroaliphatic rings, especially pyrrolidino and morpholino rings.

Specific compounds within the scope of the present invention include:

2-(R)-(1-(R)-(3,5-bis(trifluoromethyl)phenyl)ethoxy)-3-(S)-(4-fluorophenyl)-4-(4-morpholinobut-2-yn-yl)morpholine;

2-(R)-(1-(R)-(3,5-bis(trifluoromethyl)phenyl)ethoxy)-4-(4-N,N-dimethylaninobut-2-yn-yl)-3-(S)-(4-fluorophenyl)morpholine;

4-(4-azetidinylbut-2-yn-yl)-2-(R)-(1-(R)-(3,5-bis(trifluoromethyl)phenyl) ethoxy)-3-(S)-(4-fluorophenyl)morpholine;

2-(R)-(1-(R)-(3,5-bis(trifluoromethyl)phenyl)ethoxy)-3-(S)-(4-fluorophenyl)-4-(4-imidazolylbut-2-yn-yl)morpholine;

2-(R)-(1-(R)-(3,5-bis(trifluoromethyl)phenyl)ethoxy)-3-(S)-(4-fluorophenyl)-4-(4-(N-methylpiperazinyl)but-2-yn-yl)morpholine;

4-(4-bis(2-methoxyethyl)aminobut-2-yn-yl)-2-(R)-(1-(R)-(3,5-bis(trifluoromethyl)phenyl)ethoxy)-3-(S)-(4-fluorophenyl)morpholine;

2-(R)-(1-(R)-(3,5-bis(trifluoromethyl)phenyl)ethoxy)-3-(S)-(4-fluorophenyl)-4-(4-pyrrolidinobut-2-yn-yl)morpholine;

3-(S)-(4-fluorophenyl)-2-(R)-(1-(R)-(3-fluoro-5-(trifluoromethyl)phenyl) ethoxy)-4-(4-morpholinobut-2-yn-yl)morpholine;

3-(S)-(4-fluorophenyl)-4-(4-morpholinobut-2-yn-yl)-2-(R)-(1-(R)1-(3-(trifluoromethyl)phenyl)ethoxy)morpholine;

4-(4-azetidinylbut-2-yn-yl)-3-(S)-(4-fluorophenyl)-2-(R)-(1-(R)-(3-(trifluoromethyl)phenyl)ethoxy)morpholine;

2-(R)-(1-(R)-(3,5-bis(trifluoromethyl)phenyl)ethoxy)-4-(4-(N-(2-methoxyethyl)-N-methyl)aminobut-2-yn-yl)-3-(S)-phenylmorpholine;

2-(R)-(1-(R)-(3,5-bis(trifluoromethyl)phenyl)ethoxy)-4-(4-(N-cyclopropyl-N-(2-methoxyethyl)amino)but-2-yn-yl)-3-(S)-phenylmorpholine;

2-(R)-(1-(R)-(3,5-bis(trifluoromethyl)phenyl)ethoxy)-4-(4-(N-isopropyl-N-(2-methoxyethyl)amino)but-2-yn-yl)-3-(S)-phenylmorpholine;' and pharmaceutically acceptable salts thereof.

Further preferred compounds within the scope of the present invention include:

4-(4-(N,N-dimethylamino)but-2-yn-yl)-3-(S)-(4-fluorophenyl)-2-(R)-(1-(S)-(3-fluoro-5-(trifluoromethyl)phenyl-2-hydroxyethoxy)morpholine;

4-(4-azetidinylbut-2yn-yl)-3-(S)-(4-fluorophenyl)-2-(R)-(1-(S)-(3-fluoro-5-(trifluoromethyl)phenyl)-2-hydroxyethoxy)morpholine;

2-(R)-(1-(S)-(3,5-bis(trifluoromethyl)phenyl)-2-hydroxyethoxy)-4-(4-(N,N-dimethylamino)but-2-yn-yl)-3-(S)-(4-fluorophenyl)morpholine;

4-(4-azetidinylbut-2-yn-yl)-2-(R)-(1-(S)-(3,5-bis(trifluoromethyl)phenyl-2-hydroxyethoxy)-3-(S)-(4-fluorophenyl)morpholine;

-4-(4-N-bis(2-methoxy)ethyl-N-methylamino)but-2-yn-yl)-2-(R)-(1-(R)-(3,5-bis(trifluoromethyl)phenyl)ethoxy)-3-(S)-(4-fluorophenyl)morpholine;

2-(R)-(1-(R)-(3,5-bis(trifluoromethyl)phenyl)ethoxy)-3-(S)-(4-fluorophenyl)-4-(4-(2-(S)-(methoxymethyl)pyrrolidino)but-2-yn-yl)morpholine;

4-(4-(7-azabicyclo[2.2.1]heptano)but-2-yn-yl)-2-(R)-(1-(R)-(3,5-bis(trifluoromethyl)phenyl)ethoxy)-3-(S)-(4-fluorophenyl)morpholine;

2-(R)-(1-(R)-(3,5-bis(trifluoromethyl)phenyl)ethoxy)-4-(4-diisopropylaminobut-2-yn-yl)-3-(S)-(4-fluorophenyl)morpholine;

2-(R)-(1-(R)-(3-fluoro-5-(trifluoromethyl)phenyl)ethoxy)-4-(4-(2-(S)-(methoxymethyl)pyrrolidino)but-2-yn-yl)-3-(S)-phenylmorpholine;

2-(R)-(1-(R)-(3,5-bis(trifluoromethyl)phenyl)ethoxy)-3-(S)-(4-fluorophenyl)-4-(4-(2-(S)-(hydroxymethyl)pyrrolidino)but-2-yn-yl)morpholine; and pharmaceutically acceptable salts thereof.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts such as those formed with hydrochloric acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The pharmaceutically acceptable salts of the present invention may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds according to the invention have at least three asymmetric centres, and may accordingly exist both as enantiomers and as diastereoisomers. It is to be understood that all such isomers and mixtures thereof are encompassed within the scope of the present invention.

The preferred compounds of the formula (I), and (Ia) will have the 2- and 3- substituent cis and the preferred stereochemistry at the 2-position is that possessed by the compound of Example 1 (i.e. 2-(R)-), the preferred stereochemistry of the 3-position is that possessed by the compound of Example 1 (i.e. 3-(S)), and the preferred stereochemistry of the carbon to which the group Y is attached is either (R) when Y is $C_{1-4}$alkyl (e.g. methyl) or (S) when Y is $C_{1-4}$alkyl substituted by hydroxy (e.g. $CH_2OH$). Thus for example as shown in formula (Ib)

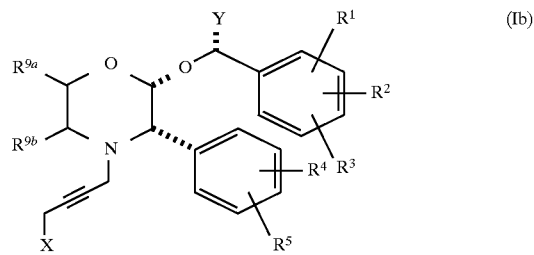

The present invention further provides pharmaceutical compositions comprising one or more compounds of formula (I) in association with a pharmaceutically acceptable carrier.

Preferably the compositions according to the invention are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a compound of formula (I), as the active ingredient, in association with a surface-active agent (or wetting agent or surfactant) or in the form of an emulsion (as a water-in-oil or oil-in-water emulsion).

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example gylcerol or glucose, to adjust the tonicity of the emulsion. Suitable emulsions will typically contain up to 20% oil, for example, between 5 and 20%. The fat emulsion will preferably comprise fat droplets between 0.1 and 1.0 $\mu$m, particularly 0.1 and 0.5 $\mu$m, and have a pH in the range of 5.0 to 8.0.

Particularly preferred emulsion compositions are those prepared by mixing a compound of formula (I) with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention futher provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; epilepsy; neurodegenerative disorders such as dementia, including AIDS related dementia, senile dementia of the Alzheimer type, Alzheimer's disease and Down's syndrome; demyelinating diseases such as multiple sclerosis (MS) and amyotrophic lateral sclerosis (ALS; Lou Gehrig's disease) and other neuropathological disorders such as peripheral neuropathy, for example AIDS related neuropathy, diabetic and chernotherapy-induced neuropathy, and postherpetic and other neuralgias; neuronal damage, such as cerebralischemic damage and cerebral edema in cerebrovascular disorders; small cell carcinomas such as small cell lung cancer; respiratory diseases, particularly those associated with excess mucus secretion such as chronic obstructive airways disease, bronchopneumonia, chronic bronchitis, asthma, and bronchospasm; airways diseases modulated by neurogenic inflammation; diseases characterised by neurogenic mucus secretion, such as cystic fibrosis; diseases associated with decreased glandular secretions, including lacrimation, such as Sjogren's syndrome, hyperlipoproteinemias IV and V, hemocromatosis, sarcoidosis, and amyloidosis; inflammatory diseases such as inflammatory bowel disease, psoriasis, fibrositis, ocular inflammation, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, dry eye syndrome, and the like; ophthalmic conditions associated with cell proliferation such as proliferative vitreoretinopathy; cutaneous diseases such as contact dermatitis, atopic dermatitis, urticaria, and other eczematoid dermatitis; addiction disorders including the withdrawal response produced by chronic treatment with, or abuse of, drugs such as benzodiazepines, opiates, cocaine, alcohol and nicotine; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosus; gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed, post-operative, late phase or anticipatory emesis such as emesis induced by chemotherapy, radiation, toxins, viral or bacterial infections, pregnancy, vestibular disorders, motion, surgery, migraine, opioid analgesics, and variations in intercranial pressure, in particular, for example, drug or radiation induced emesis or post-operative nausea and vomiting; disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, migraine and Reynaud's disease; and pain or nociception, for example, dental pain and that attributable to or associated with any of the foregoing conditions, especially the transmission of pain in migraine.

Hence, the compounds of the present invention may be of use in the treatment of physiological disorders associated with excessive stimulation of tachykinin receptors, especially neurokinin-1 receptors, and as neurokinin-1 antagonists for the control and/or treatment of any of the aforementioned clinical conditions in mammals, including humans.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed, post-operative, late phase or anticipatory emesis, such as emesis or nausea induced by chemotherapy, radiation, toxins, such as metabolic or microbial toxins, viral or bacterial infections, pregnancy, vestibular disorders, motion, mechanical stimulation, gastrointestinal obstruction, reduced gastrointestinal motility, visceral pain, psychological stress or disturbance, high altitude, weightlessness, opioid analgesics, intoxication, resulting for example from consumption of alcohol, surgery, migraine, and variations in intercranial pressure. Most especially, the compounds of formula (I) are of use in the treatment of emesis induced by antineoplastic (cytotoxic) agents including those routinely used in cancer chemotherapy.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *"Nausea and Vomiting: Recent Research and Clinical Advances"*, Eds. J. Kuucharczyk et al, CRC Press Inc., Boca Raton, Fla., USA (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-HT$_3$ antagonist, such as ondansetron, granisetron or tropisetron, or other anti-emetic medicaments, for example, a dopamine antagonist such as metoclopramide or GABAs receptor agonists such as baclofen. Additionally, a compound of formula (I) may be administered in combination with an anti-inflammatory corticosteroid, such as dexamethasone, triamcinolone, triamcinolone acetonide, flunisolide, budesonide, or others such as those disclosed in U.S. Pat. Nos. 2,789.118, 2,990,401, 3,048,581, 3,126,375, 3,929, 768, 3,996,359, 3,928,326 and 3,749,712. Dexamethasone (Decadron™) is particularly preferred. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

When tested in the ferret model of cisplatin-induced emesis described by F. D. Tattersall et al, in *Eur. J. pharmacol.*, (1993) 250, R5–R6, the compounds of the present invention were found to attenuate the retching and vomiting induced by cisplatin.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis, headache and especially migraine.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the the treatment or prevention of physiological disorders associated with an excess of tachykinins, especially substance P, which method comprises administration to a patient in need thereof of a tachykinin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor antagonist or tachykinin antagonist which acts at NK-2 receptors. The compound of formula (I) and the bronchodilator may be administered to a patient simultaneously, sequentially or in combination.

Likewise, a compound of the present invention may be employed with a leukotriene antagonists, such as a leukotriene D$_4$ antagonist such as a compound selected from those disclosed in European patent specification nos. 0 480 717 and 0 604 114 and in U.S. Pat. Nos. 4,859,692 and 5,270, 324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

It will be appreciated that for the treatment or prevention of migraine, a compound of the present invention may be used in conjunction with other anti-migraine agents, such as ergotamines or 5-HT$_1$ agonists, especially sumatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an antiinflammatory agent such as a bradykinin receptor antagonist.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis using an injectable formulation, a suitable dosage level is about 0.001 to 10 mg/kg per day, preferably about 0.005 to 5 mg/kg per day, and especially 0.01 to 1 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

According to one general process (A), the compounds of formula (I) may be prepared from compounds of formula (II)

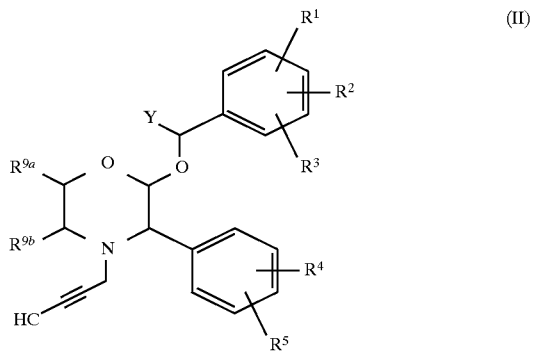

wherein $R^1$, $R^2$, $R^3$, $R^4$, $R^5$, $R^{9a}$, $R^{9b}$ and Y are as defined in relation to formula (I) by reaction with formaldehyde followed by the desired amine of formula $HNR^6R^7$, in the presence of a suitable catalyst, for example, copper (I) chloride.

This reaction may be performed in a conventional manner, for example in a solvent such as an ether, for example, dioxan, at an elevated temperature between 50° C. and 100° C., for example, at about 80° C.

According to another process (B), the compounds of formula (I) may be prepared from compounds of formula (III)

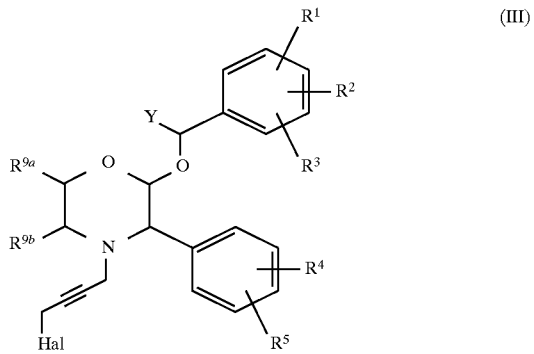

wherein $R^1$, $R^2$, $R^3$, $R^4$, $R^5$, $R^{9a}$, $R^{9b}$ and Y are as defined in relation to formula (I) and Hal is a halogen atom such as chlorine, bromine or iodine, by reaction with an amine of formula $HNR^6R^7$ or imidazole (preferably in the form of its sodium salt) in the presence of a base.

Suitable bases of use in the reaction include alkali metal carbonates such as, for example, potassium carbonate. The reaction is conveniently effected in a suitable organic solvent such as, for example, N,N-dimethylformamide, conveniently at room temperature.

According to another process (C), compounds of formula (I) may be prepared by the interconversion of a compound of formula (IV):

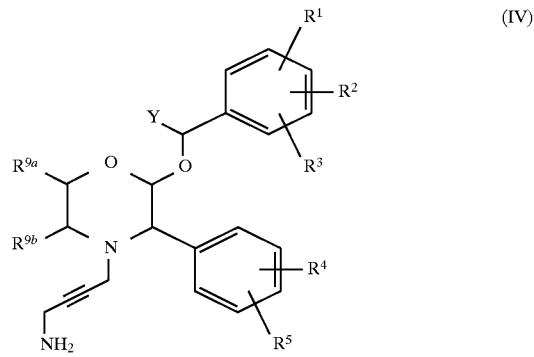

using alkyl halides of the formula $R^6$-Hal and $R^7$-Hal, or a suitable dihalide designed to form a saturated heterocyclic ring, wherein $R^6$ and $R^7$ are as previously defined, and Hal represents a halogen atom such as chlorine, bromine or iodine, in the presence of a base.

Suitable bases of use in the reaction include alkali metal carbonates, such as, for example, potassium carbonate.

The reaction is conveniently effected in a suitable organic solvent, such as, for example, N,N-dimethylformamide, conveniently at room temperature.

Suitable dihalides for forming a saturated heterocyclic ring include, for example, Hal-$(CH_2)_4$-Hal (to give a pyrrolidino ring), Hal-$(CH_2)_2O(CH_2)_2$Hal (to give a morpholino ring), or Hal-$(CH_2)_2NR^8(CH_2)_2$Hal (to give a piperazino ring).

Intermediates of formula (IV) may be prepared from intermediates of formula (II) or (III) by reaction with ammonia according to the method of either process (A) or process (B).

The compounds of formula (II) may be prepared from an intermediate of formula (V)

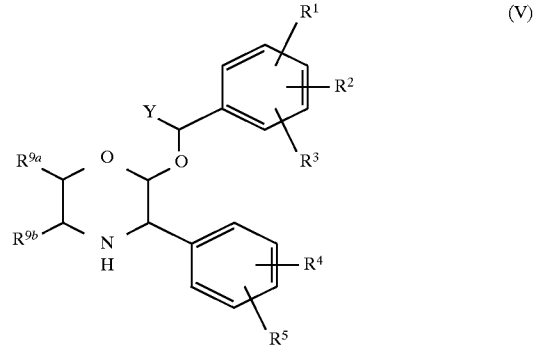

by reaction with a compound of formula (VI)

where Hal is as previously defined, in a conventional manner, for example in an organic solvent such as dimethylformamide in the presence of an acid acceptor such as potassium carbonate.

Similarly, the compounds of formula (III) may be prepared by the dropwise addition of an intermediate of formula (V) to a compound or formula (VII)

HalCHC$_2$—C≡C—CH$_2$Hal     (VII)

where Hal is as previously defined, in the presence of a base as previously described.

The compounds of formula (V) may be prepared as shown in the following scheme in which Ar$^1$ represents the R$^1$, R$^2$, R$^3$ substituted phenyl group; Ar$^2$ represents the R$^4$, R$^5$ substituted phenyl group and Ph represents phenyl:

achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

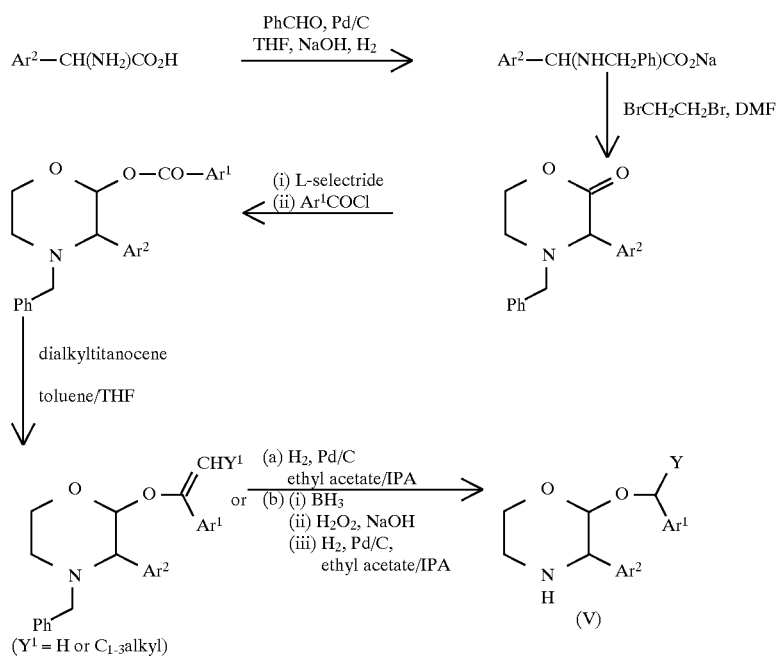

The following references describe methods which may be applied by the skilled worker to the chemical synthesis set forth above once the skilled worker has read the (disclosure herein.

(i) D. A. Evans et al., *J. Am. Chem. Soc.*, 112, 4011 (1990).
(ii) Yanagisawa, I. et al., *J. Med. Chem.*, 27, 849 (1984).
(iii) Duschinsky, R. et al., *J. Am. Chem. Soc.*, 70, 657 (1948).
(iv) Tebbe F. N. et al., *J. Am. Chem. Soc.*, 100, 3611 (1978).
(v) Petasis, N. A. et al., *J. Am. Chem. Soc.*, 112, 6532 (1990).
(vi) Takai, K. et al., *J. Org. Chem.*, 52, 4412 (1987).

The Examples disclosed herein produce predominently the preferred isomers. The unfavoured isomers are also produced on minor components. If desired they may be isolated and employed to prepare the various stereoisomers in conventional manner, for example chromatography using an appropriate chiral column. However, the skilled worker will appreciate that although the Examples have been optimized to the production of the preferred isomers, variation in solvent, reagents, chromatography etc can be readily employed to yield the other isomers.

L-Selectride is lithium tri-sec-butylborohydride.

Where they are not commercially available, the intermediates above may be prepared by the procedures described in the accompanying Examples or by alternative procedures which will be readily apparent to one skilled in the art.

During any of the above synthetic sequences it may be necessary and/or desirable to protect sensitive or reactive groups on any of the molecules concerned. This may be The exemplified compounds of this invention were tested by the methods set out at pages 36 to 39 of International Patent Specification No. WO 93/01165. The compounds were found to be active with IC50 at the NK1 receptor of less than 100 nM.

The following Examples illustrate the preparation of compounds according to the present invention:

DESCRIPTION 1

(S)-(4-Fluorophenyl)glcyine
Via Chiral Synthesis
Step A: 3-(4-Fluorophenyl)acetyl-4-(S)-benzyl-2-oxazolidinone An oven-dried, 1 L 3-necked flask, equipped with a septum, nitrogen inlet, thermometer, and a magnetic stirring bar, was flushed with nitrogen and charged with a solution of 5.09 g (33.0 mmol) of 4-fluorophenylacetic acid in 100 ml of anhydrous ether. The solution was cooled to −10° C. and treated with 5.60 ml (40.0 mmol) of triethylamine followed by 4.30 ml (35.0 mmol) of trimethylacetyl chloride. A white precipitate formed immediately. The resulting mixture was stirred at −10° C. for 40 minutes, then cooled to −78° C.

An oven-dried, 250 ml round bottom flask, equipped with a septum and a magnetic stirring bar, was flushed with nitrogen and charged with a solution of 5.31 g (30.0 mmol) of 4-(S)-benzyl-2-oxazolidinone in 40 ml of dry THF. The solution was stirred in a dry ice/acetone bath for 10 minutes, then 18.8 ml of 1.6M n-butyllithium solution in hexanes was slowly added. After 10 minutes, the lithiated oxazolidinone solution was added, via cannula, to the above mixture in the 3-necked flask. The cooling bath was removed from the resulting mixture and the temperature was allowed to rise to 0° C. The reaction was quenched With 100 ml of saturated aqueous ammonium chloride solution, transferred to a 1 l flask, and the ether and THF were removed in vacuo. The concentrated mixture was partitioned between 300 ml of methylene chloride and 50 ml of water and the layers were separated. The organic layer was washed with 100 ml of 2N aqueous hydrochloric acid solution, 300 ml of saturated aqueous sodium bicarbonate solution, dried over magnesium sulfate and concentrated in vacuo. Flash chromatography on 400 g of silica gel using 3:2 v/v hexanes/ether as the eluant afforded 8.95 g of an oil that slowly solidified on standing. Recrystallisation from 10:1 hexanes/ether afforded 7.89 g (83%) of the title compound as a white solid: mp 64°–66° C. MS (FAB): m/z 314 ($M^+$+H, 100%), 177 (M—$ArCH_2CO$+ H, 85%). 1H NMR (400 MHz, $CDCl_3$) δ2.76 (1H, dd, J=13.2, 9.2 Hz), 3.26 (dd, J=13.2, 3.2 Hz), 4.16–4.34 (4H, m), 4.65 (1H, m), 7.02–7.33 (9H, m).

Analysis Calcd. for $C_{18}H_{16}FNO_3$: C, 69.00; H, 5.15; N, 4.47; F, 6.06; Found: C, 68.86; H, 5.14; N, 4.48; F, 6.08%.

Step B: 3-((S)-Azido-(4-fluorophenyl))acetyl-4-(S)-benzyl-2-oxazolidinone

An oven-dried, 1 l 3-necked flask, equipped with a septum, nitrogen inlet, thermometer, and a magnetic stirring bar, was flushed with nitrogen and charged with a solution of 58.0 ml of 1M potassium bis(trimethylsilyl)amide solution in toluene and 85 ml of THF and was cooled to −78° C. An oven-dried 250 ml round-bottomed flask, equipped with a septum and a magnetic stirring bar, was flushed with nitrogen and charged with a solution of 7.20 g (23.0 mmol) of 3-(4-fluorophenyl)acetyl-4-(S)-benzyl-2-oxazolidinone (from Step A) in 40 ml of THF. The acyl oxazolidinone solution was stirred in a dry ice/acetone bath for 10 minutes, then transferred, via cannula, to the potassium bis (trimethylsilyl)amide solution at such a rate that the internal temperature of the mixture was maintained below −70° C. The acyl oxazolidinone flask was rinsed with 15 ml of THF and the rinse was added, via cannula, to the reaction mixture and the resulting mixture was stirred at −78° C. for 30 minutes. An oven-dried, 250 ml round-bottomed flask, equipped with a septum and a magnetic stirring bar, was flushed with nitrogen and charged with a solution of 10.89 g (35.0 mmol) of 2,4,6-triisopropylphenylsulfonyl azide in 40 ml of THF. The azide solution was stirred in a dry ice/acetone bath for 10 minutes, then transferred, via cannula, to the reaction mixture at such a rate that the internal temperature of the mixture was maintained below −70° C. After 2 minutes, the reaction was quenched with 6.0 ml of glacial acetic acid, the cooling bath was removed and the mixture was stirred at room temperature for 18 hours. The quenched reaction mixture was partitioned between 300 ml of ethyl acetate and 300 ml of 50% saturated aqueous sodium bicarbonate solution. The organic layer was separated, dried over magnesium sulfate, and concentrated in vacuo. Flash chromatography on 500 g of silica gel using 2:1 v/v, then 1:1 v/v hexanes/methylene chloride as the eluant afforded 5.45 g (67%) of the title compound as an oil. IR Spectrum (neat, $cm^{-1}$): 2104, 1781, 1702. $^1$H NMR (400 MHz, $CDCl_3$) δ2.86 (1H, dd, J=13.2, 9.6 Hz), 3.40 (1H, dd, J=13.2, 3.2 Hz), 4.09–4.19 (2H, m), 4.62–4.68 (1H, m), 6.14 (1H, s), 7.07–7.47 (9H, m).

Analysis Calcd. for $C_{18}H_{15}FN_4O_3$: C 61.01; H, 4.27; N, 15.81; F, 5.36; Found: C, 60.99; H, 4.19; N, 15.80; F, 5.34%.

Step C: (S)-Azido-(4-fluorophenyl)acetic acid

A solution of 5.40 g (15.2 mmol) of 3-((S)-azido-(4-fluorophenyl))acetyl-4-(S)-benzyl-2-oxazolidinone (from Step B) in 200 ml of 3:1 v/v THF/water was stirred in an ice bath for 10 minutes. 1.28 g (30.4 mmol) of lithium hydroxide monohydrate was added in one portion and the resulting mixture was stirred cold for 30 minutes. The reaction mixture was partitioned between 100 ml of methylene chloride and 100 ml of 25% saturated aqueous sodium bicarbonate solution and the layers were separated. The aqueous layer was washed with 2×100 ml of methylene chloride and acidified to pH 2 with 2N aqueous hydrochloric acid solution. The resulting mixture was extracted with 2×100 ml of ethyl acetate; the extracts were combined, washed with 50 ml of saturated aqueous sodium chloride solution, dried over magnesium sulfate, and concentrated in vacuo to afford 2.30 g (77%) of the title compound as an oil that was used in the following step without further purification. IR Spectrum (neat, $cm^{-1}$): 2111, 1724. $^1$H NMR (400 MHz, $CDCl_3$) δ5.06 (1H, s), 7.08–7.45 (4H, m), 8.75 (1H, br s).

Step D: (S)-(4-Fluorophenyl)glycine

A mixture of 2.30 g (11.8 mmol) of (S)-azido-(4-fluorophenyl)acetic acid (from Step C), 2.50 mg 10% palladium on carbon catalyst and 160 ml 3:1 v/v water/acetic acid was stirred under an atmosphere of hydrogen for 18 hours. The reaction mixture was filtered through Celite and the flask and filter cake were rinsed well with about 1 liter of 3:1 v/v water/acetic acid. The filtrate was concentrated in vacuo to about 50 ml of volume. 300 ml of toluene was added and the mixture concentrated to afford a solid. The solid was suspended in 1:1 v/v methanol/ether, filtered and dried to afford 1.99 g (100%) of the title compound. $^1$H NMR (400 MHz, $D_2O$+NaOD) δ3.97 (1H, s), 6.77 (2H, app t, J=8.8 Hz), 7.01 (2H, app t, J=5.6 Hz).

Via Resolution

Step A' (4-Fluorophenyl)acetyl chloride

A solution of 150 g (0.974 mol) of 4-(fluorophenyl)acetic acid and 1 ml of N,N-dimethylformamide in 500 ml of toluene at 40° C. was treated with 20 ml of thionyl chloride and heated to 40° C. An additional 61.2 ml of thionyl chloride was added dropwise over 1.5 hours. After the addition, the solution was heated at 50° C. for 1 hour, the solvent was removed in vacuo and the residual oil was distilled at reduced pressure (1.5 mmHg) to afford 150.4 g (89.5%) of the title compound, bp=68°–70° C.

Step B': Methyl 2-bromo-3-(4-fluorophenyl)acetate

A mixture of 150.4 g (0.872 mol) of 4-(fluorophenyl) acetyl chloride (from Step A') and 174.5 g (1.09 mol) of bromine was irradiated at 40°–50° C. with a quartz lamp for 5 hours. The reaction mixture was added dropwise to 400 ml of methanol and the solution was stirred for 16 hours. The solvent was removed in vacuo and the residual oil was distilled at reduced pressure (1.5 mmHg) to afford 198.5 g (92%) of the title compound, bp=106°–110° C.

Step C': Methyl (±)-(4-fluorophenyl)glycine

A solution of 24.7 g (0.1 mol) of methyl 2-bromo-2-(4-fluorophenyl)acetate (from Step B') and 2.28 g (0.01 mol) of benzyl triethylammonium chloride in 25 ml of methanol was treated with 6.8 g (0.105 mol) of sodium azide and the resulting mixture was stirred for 20 hours at room temperature. The reaction mixture was filtered; the filtrate was diluted with 50 ml of methanol and hydrogenated in the presence of 0.5 g of 10% Pd/C at 50 psi for 1 hour. The solution was filtered and the solvent removed in vacuo. The residue was partitioned between 10% aqueous sodium carbonate solution and ethyl acetate. The organic phase was washed with water, saturated aqueous sodium chloride solution dried over magnesium sulfate and concentrated in vacuo to afford 9.8 g of the title compound as an oil.

Step D': Methyl (S)-(4-fluorophenyl)glycinate

A solution of 58.4 g of methyl (±) 4-(fluorophenyl) glycinate (from Step C') in 110 ml of 7:1 v/v ethanol/water was mixed with a solution of 28.6 g (0.0799 mol) of O,O'-(+)-dibenzoyltartaric acid ((+)-DBT) (28.6 g, 0.0799 mol) in 110 ml of 7:1 v/v ethanol:water and the resulting solution was allowed to age at room temperature. Ethyl acetate (220 ml) was added after crystallisation was complete and the resulting mixture was cooled to −20° C. and filtered to afford 32.4 g of methyl (S)-(4-fluorophenyl) glycinate, (+)-DBT salt (ee=93.2%). The mother liquors were concentrated in vacuo and the free base was liberated by partitioning between ethyl acetate and aqueous sodium carbonate solution. A solution of free base, so obtained, in 110 ml of 7:1 v/v ethanol/water was mixed teeth a solution of 28.6 g (0.0799 mol) of O,O'-(−)-dibenzoyltartaric acid ((−)-DBT) (28.6 g, 0.0799 mol) in 110 ml of 7:1 v/v ethanol:water and the resulting solution was allowed to age at room temperature. Ethyl acetate (220 ml) was added after crystallisation was complete and the resulting mixture was cooled to −20° C. and filtered to afford 47.0 g of methyl (R)-(4-fluorophenyl)glycinate, (−)-DBT salt (ee=75.8%). Recycling of the mother liquors and addition of (+)-DBT gave a second crop of 7.4 g of (S)-(4-fluorophenyl)glycinate, (+)-DBT salt (ee=96.4%). The two crops of the (S)-amino ester (39.8 g) were combined in 200 ml of 7:1 v/v ethanol/water, heated for 30 minutes and cooled to room temperature. Addition of ethyl acetate, cooling, and filtration afforded 31.7 g of (S)-(4-fluorophenyl)glycinate, (+)-DBT salt (ee>98%). Enantiomeric excess was determined by chiral HPLC (Crownpak CR(+) 5% MeOH in aq $HClO_4$ pH2 1.5 ml/min 40° C. 200 nm).

A mixture of 17.5 g of (S)-(4-fluorophenyl)glycinate, (+)-DBT salt and 32 ml of 5.5N HCl (32 ml) was heated at reflux for 1.5 hours. The reaction mixture was concentrated in vacuo and the residue was dissolved in 40 ml of water. The aqueous solution was washed (3×30 ml of ethyl acetate) and the layers were separated. The pH of the aqueous layer was adjusted to 7 using ammonium hydroxide and the precipitated solid was filtered to afford 7.4 g of the title compound (ee=98.8%).

DESCRIPTION 2

4-Benzyl-3-(S)-(4-fluorophenyl)-2-morpholinone

Step A: N-Benzyl-(S)-(4-fluorophenyl)glycine

A solution of 1.87 g (11.05 mmol) of (S)-(4-fluorophenyl)-glycine (from Description 1) and 1.12 ml (11.1 mmol) of benzaldehyde in 11.1 ml of 1N aqueous sodium hydroxide solution and 11 ml of methanol at 0° C. was treated with 165 mg (4.4 mmol) of sodium borohydride. The cooling bath was removed and the resulting mixture was stirred at room temperature for 30 minutes. Second portions of benzaldehyde (1.12 ml (11.1 mmol)) and sodium borohydride (165 mg (4.4 mmol) were added to the reaction mixture and stirring was continued for 1.5 hours. The reaction mixture was partitioned between 100 ml of ether and 50 ml of water and the layers were separated. The aqueous layer was separated and filtered to remove a small amount of insoluble material. The filtrate was acidified to pH 5 with 2N aqueous hydrochloric acid solution and the solid that had precipitated was filtered, rinsed well with water, then ether, and dried to afford 1.95 g of the title compound. $^1$H NMR (400 MHz, $D_2O$+NaOD) δ3.33 (2H, AB q, J=8.4 Hz), 3.85 (1H, s), 6.79–7.16 (4H, m).

Step B: 4-Benzyl-3-(S)-(4-fluorophenyl)-2-morpholinone

A mixture of 1.95 g (7.5 mmol) of N-benzyl (S)-(4-fluorophenyl)glycine, 3.90 ml (22.5 mmol) of N,N-diisopropyl-ethylamine, 6.50 ml (75.0 mmol) of 1,2-dibromoethane and 40 ml of N,N-dimethylformamide was stirred at 100° C. for 20 hours (dissolution of all solids occurred on warming). The reaction mixture was cooled and concentrated in vacuo. The residue was partitioned between 250 ml of ether and 100 ml of 0.5N potassium hydrogen sulfate solution and the layers were separated. The organic layer was washed with 100 ml of saturated aqueous sodium bicarbonate solution, 3×150 ml of water, dried over magnesium sulfate, and concentrated in vacuo. Flash chromatography on 125 g of silica gel using 3:1 v/v hexanes/ether as the eluant afforded 1.58 g (74%) of the title compound as an oil. $^1$H NMR (400 MHz, $CDCl_3$) δ2.65 (1H, dt, J=3.2, 12.8 Hz), 3.00 (1H, dt, J=12.8, 2.8 Hz), 3.16 (1H, d, J=13.6 Hz), 3.76 (1H, d, J=13.6 Hz), 4.24 (1H, s), 4.37 (1H, dt, J=13.2, 3.2 Hz), 4.54 (1H, dt, J=2.8, 13.2 Hz), 7.07–7.56 (9H, m).

DESCRIPTION 3

4-Benzyl-2-(R)-(3,5-bis(trifluoromethyl) benzoyloxy)-3-(S)-(4-fluorophenyl)morpholine A solution of 2.67 g (10.0 mmol) of 4-benzyl-3-(S)-(4-fluorophenyl)-2-morpholinone (Description 2) in 40 ml of dry THF was cooled to −78° C. The cold solution was treated with 12.5 ml of 1.0 ml L-Selectride® solution in THF, maintaining the internal reaction temperature below −70° C. The resulting solution was stirred cold for 45 minutes and the reaction was charged with 3.60 ml(20.0 mmol) of 3,5-bis(trifluoromethyl)benzoyl chloride. The resulting yellow mixture was stirred cold for 30 minutes and the reaction was quenched with 50 ml of saturated aqueous sodium bicarbonate solution. The quenched mixture was partitioned between 300 ml of ether and 50 ml of water and the layers were separated. The organic layer was dried over magnesium sulfate. The aqueous layer was extracted with 300 ml of ether; the extract was dried and combined with the original organic layer. The combined organics were concentrated in vacuo. Flash chromatography on 150 g of silica gel using 37:3 v/v hexanes/ether as the eluant afforded 4.06 g (80%) of the title compound as a solid.

$^1$H NMR (200 MHz, $CDCl_3$) δ2.50 (1H, dt, J=3.4, 12.0 Hz), 2.97 ($^1$H, app d, J=12.0 Hz), 2.99 (1H, d, J=13.6 Hz), 3.72–3.79 (1H, m), 3.82 (1H, d, J=2.6 Hz), 4.00 (1H, d, J=13.6 Hz), 4.20 (dt, J=2.4, 11.6 Hz), 6.22 (1H, d, J=2.6 Hz), 7.22.7.37 (7H, m), 7.57 (2H, app d, J=6.8 Hz), 8.07 (1H, s), 8.47 (2H, s). MS (FAB) m/z 528 (M+H, 25%), 270 (100%).

Analysis Calcd. for $C_{26}H_{20}F_7NO_3$: C, 59.21; H, 3.82; N, 2.66; F, 25.21; Found: C, 59.06; H, 4.05; N. 2.50; F, 25.18%.

DESCRIPTION 4

4-Benzyl-2-(R)-(1-(3,5-bis(trifluoromethyl)phenyl) ethenyloxy)-3-(S)-(4-fluorophenyl)morpholine Step A: Dimethyl titanocene A solution of 2.49 g (10.0 mmol) of titanocene dichloride in 50 ml of ether in the dark at 0° C. was treated with 17.5 ml of 1.4M methyllithium solution in ether maintaining the internal temperature below 5° C. The resulting yellow/orange mixture was stirred at room temperature for 30 minutes and the reaction was quenched by slowly adding 25 g of ice. The quenched reaction mixture was diluted with 50 ml of ether and 25 ml of water and the layers were separated. The organic layer was dried over magnesium sulfate and concentrated in vacuo to afford 2.03 g (98%) of the title compound as a light-sensitive solid. The dimethyl titanocene could be stored as a solution in toluene at 0° C. for at least 2 weeks without apparent chemical degradation. $^1$H NMR (200 MHz, $CDCl_3$) δ−0.15 (6H, s), 6.06 (10H, s).

Step B: 4-Benzyl-2-(R)-(1-(3,5-bis(trifluoromethyl)Phenyl) ethenyloxy)-3-(S)-(4-fluorophenyl)morpholine A solution of the compound of Description 3 (2.50 g, 4.9 mmol) and 2.50 g (12.0 mmol) of dimethyl titanocene (from Step A) in 35 ml of 1:1 v/v THF/toluene was stirred in an oil bath at 80° C. for 16 hours. The reaction mixture was cooled and concentrated in vacuo. Flash chromatography on 150 g of silica gel using 3:1 v/v hexanes/methylene chloride as the eluant afforded 1.71 g (69%) of the title compound as a solid. An analytical sample was obtained via recrystallisation from isopropanol: $^1$H NMR (400 MHz, CDCl$_3$) δ2.42 (1H, dt, J=3.6, 12.0 Hz), 2.90 (1H, app d, J=12.0 Hz), 2.91 (1H, d, J=13.6 Hz), 3.62–3.66 (1H, m), 3.72 (1H, d, J=2.6 Hz), 3.94 (1H, d, J=13.6 Hz), 4.09 (1H, dt, J=2.4, 12.0 Hz), 4.75 (1H, d, J=3.2 Hz), 4.82 (1H, d, J=3.2 Hz), 5.32 (1H, d, J=2.6 Hz), 7.09 (2H, t, J=8.8 Hz), 7.24–7.33 (5H, m), 7.58–7.62 (2H, m), 7.80 (1H, s), 7.90 (2H, s);

MS (FAB) 526 (M+H, 75%), 270 (100%).

Analysis Calcd. for C$_{27}$H$_{22}$F$_7$NO$_2$: C, 61.72; H, 4.22; N, 2.67; F, 25.31; Found: C, 61.79; H, 4.10; N, 2.65; F, 25.27%.

DESCRIPTION 5

2-(R)-(1(R)-(3,5-Bis(trifluoromethyl)phenyl)ethoxy) -3-(S)-(4-fluorophenyl)morpholine The compound of Description 4 (4.0 g) was dissolved in ethyl acetate (50 ml) and isopropanol (16 ml). To this solution was added palladium on charcoal (1.5 g) and the mixture was hydrogenated at 40 psi for 36 h. The catalyst was removed by filtration through Celite and the solvents were removed in vacuo. The residue was purified by flash chromatography on silica using 100% ethyl acetate and then 1–10% methanol in ethyl acetate. This afforded isomer A 500 mg (15%) and isomer B 2.6 g (80%) as clear oils—isomer B crystallised on standing. For the title compound: $^1$H NMR (400 MHz, CDCl$_3$) δ1.16 (3H, d, J=6.8 MHz), 1.80 (1H, br s), 3.13 (1H, dd, J=3.2, 12.4 Hz), 3.23 (1H, dt, J=3.6, 12.4 Hz), 3.63 (1H, dd, J=2.4, 11.2 Hz), 4.01 (1H, d, J=2.4 Hz), 4.13 (1H, dt, J=3.2, 12.0 Hz), 4.42 (1H, d, J=2.4 Hz), 4.19 (1H, q, J=6.8 Hz), 7.04–7.09 (2H, m), 7.27–7.40 (4H, m), 7.73 (1H

MS (FAB) 438 (M+H, 75%), 180 (100%).

HCl salt formation. To a solution of the free base (0.77 g) in diethyl ether (10 ml) was added 1M-HCl in methanol (1.75 ml). The solution was evaporated to dryness and on addition of diethyl ether crystals formed. The solution was filtered and the residue washed with diethyl ether to give the title compound hydrochloride salt mp 248°–250° C.

Analysis Calcd. for C$_{20}$H$_{18}$F$_7$NO$_2$.HCl: C, 50.70; H, 4.04; N, 2.96; Cl, 7.48; Found: C, 50.46; H, 3.85; N, 3.01; Cl, 7.31%.

DESCRIPTION 6

2-(R)-(1-(R)-(3,5-Bis(trifluoromethyl)phenyl) ethoxy)-4-(4-chlorobut-2-ynyl)-3-(S)-(4-fluorophenyl)morpholine A solution of the product of Description 5 (free base, 5 g) in N,N-dimethylformamide (20 ml) was slowly added to a heated (50° C.) solution of 1,4-dichlorobut-2-yne (2.2 ml) and potassium carbonate (4.8 g) in N,N-dimethylformamide (20 ml). The solution was heated for a further 5 h at 50° C. and then the solvent removed in vacuo. To the residue was added water (400 ml) and the product extracted into ethyl acetate (3×150 ml). The combined organic phase was washed with water, saturate brine and dried (MgSO4). The solvent was removed in vacuo and the residue chromatographed on silica gel (eluting with 10% ethyl acetate in petroleum ether bp 60°–80° C.) to give the title compound as a colourless oil.

$^1$H NMR (250 MHz, CDCl$_3$) δ1.41 (3H, d, J=6.6 Hz), 2.80 (1H, app. t, J=10.8 Hz), 2.87 (1H, td, J=3.5 Hz, 11.7 Hz), 3.22 (2H, t, J=1.9 Hz), 3.52 (1H, d, J=2.8 Hz), 3.68 (1H, d, J=1.4 Hz, 11.1 Hz), 4.00 (2H, t, J=1.9 Hz), 4.22–4.32 (2H, m), 4.81 (1H, q, J=6.6 Hz), 6.96 (2H, t, J=8.7 Hz), 7.10 (2H, s), 7.31 (2H, br s), 7.56 (1H, s). m/z (CI$^+$) 524 (M+H, 100%).

DESCRIPTION 7

2-(R)-(1-(R)-(3,5-Bis(trifluoromethyl)phenyl) ethoxy)-3-(S)-(4-fluorophenyl)-4-(prop-2-ynyl) morpholine Propargyl bromide (1.9 ml) was added to a stirred mixture of the compound of Description 5 (5 g) and potassium carbonate (4.76 g) in dry dimethylformamide at 23° C. After 15 min the reaction mixture was diluted with water (250 ml) and extracted with ethyl acetate (3×100 ml). The combined organic phases were washed with brine (1×100 ml) then dried (K$_2$CO$_3$) and concentrated to leave an oil. This was purified by chromatography on silica using ethyl acetate in hexane (1:9 then 1:4) as eluent to afford the title compound as an oil. $^1$H NMR (250 MHz, CDCl$_3$) δ1.50 (3H, d, J=6.6 Hz), 2.21 (1H, s), 2.84 (1H, d, J=11.1 Hz), 2.97 (1H, td, J=3.2, 11.7 Hz), 3.26 (2H, d, J=1.8 Hz), 3.62 (1H, d, J=2.2 Hz), 3.71 (1H, dd, J=2.3, 11.1 Hz), 4.33 (2H, m), 4.89 (1H, q, J=6.6 Hz), 7.03 (2H, t, J=8.6 Hz), 7.18 (2H, s), 7.38 (2H, br s), 7.63 (1H, s). MS (CI+) m/z 476 (MH, 100%).

DESCRIPTION 8

4-Benzyl-3-(S)-(4-fluorophenyl)-2-(R)-(3-fluoro-5-(trifluoromethyl) benzoyloxy)morpholine The title compound was prepared from the reaction of the compound of Description 2 with 3-fluoro-5-(trifluoromethyl)benzoyl chloride according to the procedure illustrated in Description 3. $^1$H NMR (360 MHz, CDCl$_3$) δ2.50 (1H, dt, J=3.3, 12.0 Hz), 2.96 (1H, d, J=12.0 Hz), 2.98 (1H, d, J=13.6 Hz), 3.75 (1H, dd, J=1.7, 11.5 Hz), 3.80 (1H, d, J=2.5 Hz), 3.92 (1H, d, J=13.6 Hz), 4.19 (1H, dt, J=2.1, 12.0 Hz), 6.20 (1H, d, J=2.5 Hz), 6.99 (2H, t, J=8.7 Hz), 7.2–7.37 (5H, m), 7.51–7.55 (3H, m), 7.89 (1H, d, J=8.4 Hz), 8.09 (1H, s). MS (CI+) m/z 478 (M$^+$+1, 100%).

Analysis Calcd. for C$_{25}$H$_{20}$F$_5$NO$_3$: C, 62.88; H, 4.23; N, 2.93; Found: C, 62.59; H, 4.03; N, 3.07%.

DESCRIPTION 9

4-Benzyl-3-(S)-(4-fluorophenyl)-2-(R)-(1-(3-fluoro-5-(trifluoromethyl) phenyl)ethenyloxy)morpholine The title compound was prepared in 85% yield from the compound of Description 6 according to the procedure illustrated in Description 4.

$^1$H NMR (360 MHz, CDCl$_3$) δ2.42 (1H, dt, J=3.6, 12.0 Hz), 2.90 (1H, d, J=12.0 Hz), 2.91 (1H, d, J=13.6 Hz), 3.60–3.62 (1H, m), 3.72 (1H, d, J=2.6 Hz), 3.92 (1H, d, J=13.6 Hz), 4.09 (1H, dt, J=2.4, 12.0 Hz), 4.67 (1H, d, J=2.9 Hz), 4.76 (1H, d, J=2.9 Hz), 5.28 (1H, d, J=2.6 Hz), 7.07 (2H, t, J=8.7 Hz), 7.2–7.37 (7H, m), 7.53 (1H, s), 7.57–7.61 (2H, m). MS (CI+) 476 (M+1, 100%).

DESCRIPTION 10

3-(S)-(4-Fluorophenyl)-2-(R)-(1-(R)-(3-fluoro-5-(trifluoromethyl) phenyl)ethoxy)morpholine The compound of Description 9 was hydrogenated according to the method illustrated in Description 5. This afforded a mixture of 2 epimeric products isomer A and isomer B (the major product) as clear oils. For the title compound: $^1$H NMR (360 MHz, CDCl$_3$) δ1.42 (3H, d, J=6.6 Hz), 1.91 (1H, s), 3.11 (1H, dd, J=3.2, 12.4 Hz), 3.22 (1H, dt, J=3.6, 12.4 Hz), 3.58–3.62 (1H, m), 4.01 (1H, d, J=2.3 Hz), 4.11 (1H, dt, J=3.2, 12.0 Hz), 4.41 (1H, d, J=2.3 Hz), 4.80 (1H, q, J=6.6 Hz), 6.41 (1H, d, J=9.2 Hz), 6.86 (1H, s), 7.02 (2H, t, J=8.7 Hz), 7.08 (2H, d, J=9.2 Hz), 7.21–7.26 (2H, m). MS (CI+) m/z 387 (M+1, 100%).

Analysis Calcd. for C$_{19}$H$_{18}$F$_5$NO$_2$: C, 58.91; H, 4.69; N, 3.62; Found: C, 58.88; H, 4.81; N, 3.76%.

DESCRIPTION 11

4-(4-Chlorobut-2-yn-yl)-3-(S)-(4-fluorophenyl)-2-(R)-(1)-(3-fluoro-5-(trifluoromethyl)phenyl)ethoxy) morpholine This compound was prepared from the compound of Description 10 following the procedure illustrated in Description 6. $^1$H NMR (250 MHz, CDCl$_3$) δ1.43 (3H, d, J=6.6 Hz), 2.80–2.90 (1H, m), 2.94 (1H, dt, J=11.7, 3.5 Hz), 3.32 (2H, t, J=2.0 Hz), 3.60 (1H, d, J=2.8 Hz), 3.67–3.74 (1H, m), 4.14 (2H, d, J=2.0 Hz), 4.33 (2H, dt, J=11.3, 3.3 Hz), 4.78 (1H, q, J=6.6 Hz), 6.39 (1H, d, J=9.1 Hz), 6.81 (1H, s), 7.01–7.08 (3H, m), 7.36 (2H, br s). MS (CI+) m/z 474/476 (M+1, 100/35%).

DESCRIPTION 12

4-Benzyl-3-(S)-(4-fluorophenyl)-2-(R)-(3-(trifluoromethyl)benzoyloxy) morpholine The title compound was prepared from the reaction of the compound of Description 2 with 3-(trifluoromethyl)benzoyl chloride according to the procedure illustrated in Description 3. $^1$H NMR (360 MHz, CDCl$_3$) δ2.48 (1H, dt, J=12.0, 3.5 Hz), 2.94 (1H, d, J=13.6 Hz), 3.73 (1H, app.d, J=11.4 Hz), 3.78 (1H, d, J=2.7 Hz), 3.91 (1H, d, J=13.6 Hz), 4.21 (1H, dt, J=11.7, 2.4 Hz), 6.20 (1H, d, J=2.8 Hz), 6.97 (2H, t, J=8.7 Hz), 7.25–7.37 (5H, m), 7.53 (2H, m), 7.61 (1H, t, J=7.8 Hz), 7.84 (1H, d, J=8.0 Hz), 8.21 (1H, d, J=7.8 Hz), 8.30 (1H, s). MS (CI$^+$) m/z 460 (M+1, 100%).

DESCRIPTION 13

4-Benzyl-3-(S)-(4-fluorophenyl)-2-(R)-(1-(3-(trifluoromethyl)phenyl) ethenyloxy)morpholine The title compound was prepared from the compound of Description 12 according to the procedure illustrated in Description 4. $^1$H NMR (360 MHz, CDCl$_3$) δ2.40 (1H, dt, J=11.9, 3.6 Hz), 2.87 (1H, app. d, J=11.8 Hz), 2.89 (1H, d, J=13.5 Hz), 3.62 (1H, app.d, J=11.5 Hz), 3.70 (1H, d, J=2.7 Hz), 3.91 (1H, d, J=13.5 Hz), 4.12 (1H, dt, J=11.7, 2.4 Hz), 4.62 (1H, d, J=2.7 Hz), 4.74 (1H, d, J=2.7 Hz), 5.30 (1H, d, J=2.7 Hz), 7.07 (2H, t, J=8.7 Hz), 7.21–7.32 (5H, m), 7.40 (1H, t, J=7.8 Hz), 7.53–7.63 (4H, m), 7.74 (1H, s). MS (CI$^+$) m/z 458 (M+1, 100%).

DESCRIPTION 14

3-(S)-(4-Fluorophenyl)-2-(R)-(1-(R)-(3-(trifluoromethyl)phenyl)ethoxy) morpholine The compound of Description 13 was hydrogenated according to the method illustrated in Description 5. This afforded a mixture of 2 epimeric products isomer A and isomer B in approximately equal mass as yellow oils. The title compound (isomer B): $^1$H NMR (360 MHz, CDCl$_3$) 1.43 (3H, d, J=6.6 Hz), 3.11 (1H, dd, J=12.6, 2.9 Hz), 3.22 (1H, dt, J=12.4, 3.7 Hz), 3.60 (1H, dd, J=11.1, 2.8 Hz), 3.99 (1H, d, J=2.2 Hz), 4.13 (1H, dt, J=11.6, 3.2 Hz), 4.42 (1H, d, J=2.2 Hz), 4.81 (1H, q, J=6.6 Hz), 6.84 (1H, d, J=7.8 Hz), 6.96–7.03 (3H, m), 7.16–7.27 (3H, m), 7.38 (1H, d, J=7.5 Hz). MS (CI$^+$) m/z 370 (M+1, 100%).

Analysis Calcd. for C$_{19}$H$_{19}$F$_4$NO$_2$: C, 61.77; H, 5.20; N, 3.79; Found: C, 61.60; H, 5.16; N, 3.95%.

DESCRIPTION 15

4-(4-Chlorobut-2-ynyl)-3-(S)-(4-fluorophenyl)-2-(R)-(1-(R)-(3-trifluoromethyl)phenyl)ethoxy) morpholine This compound was prepared from the compound of Description 14 following the procedure illustrated in Description 6. $^1$H NMR (360 MHz, CDCl$_3$) δ1.45 (3H, d, J=6.6 Hz), 2.85 (1H, br d, J=10.5 Hz), 2.93 (1H, dt, J=11.7, 3.6 Hz), 3.30 (2H, d, J=1.8 Hz), 3.58 (1H, d, J=2.7 Hz), 3.67–3.72 (1H, m), 4.13 (2H, d, J=1.9 Hz), 4.31–4.39 (2H, m), 4.79 (1H, q, J=6.6 Hz), 6.81 (1H, d, J=7.8 Hz), 6.97–7.05 (4H, m), 7.15 (1H, t, J=7.7 Hz), 7.35 (2H, d, J=7.8 Hz). MS (CI+) m/z 456/458 (M+1, 100/38%).

DESCRIPTION 16

4-Benzyl-3-(S)-phenyl-2-morpholinone

Step A: N-Benzyl-(S)-phenylglycine

A solution of 1.51 g (10.0 mmol) of (S)-phenylglycine in 5 ml of 2N aqueous sodium hydroxide solution was treated with 1.0 ml (10.0 mmol) of benzaldehyde and stirred at room temperature for 20 minutes. The solution was diluted with 5 ml of methanol, cooled to 0° C., and carefully treated with 200 mg (5.3 mmol) of sodium borohydride. The cooling bath was removed and the reaction mixture was stirred at room temperature for 1.5 hours. The reaction was diluted with 20 ml of water and extracted with 2×25 ml of methylene chloride. The aqueous layer was acidified with concentrated hydrochloric acid to pH 6 and the solid that precipitated was filtered, washed with 50 ml of water, 50 ml of 1:1 v/v methanol/ethyl ether and 50 ml of ether, and dried to afford 1.83 g (76%) of product, mp 230°–232° C.

Analysis Calcd. for C$_{15}$H$_{15}$NO$_2$: C, 74.66; H, 6.27; N, 5.81; Found: C, 74.17; H, 6.19; N, 5.86%.

Step B: 4-Benzyl-3-(S)-phenyl-2-morpholinone

A mixture of 4.00 g (16.6 mmol) of N-benzyl-(S)-phenylglycine (from Step A) 5.00 g (36.0 mmol) of potassium carbonate, 10.0 ml of 1,2-dibromoethane and 25 ml of N,N-dimethylformamide was stirred at 100° C. for 20 hours. The mixture was cooled and partitioned between 200 ml of ethyl ether and 100 ml of water. The layers were separated and the organic layer was washed with 3×50 ml of water, dried over magnesium sulfate and concentrated in vacuo. The residue was purified by flash chromatography on 125 g of silica gel eluting with 9:1 v/v, then 4:1 hexanes/ethyl ether to afford 2.41 g (54%) of the product as a solid, mp 98°–100° C. $^1$H NMR (250 MHz, CDCl$_3$) δ2.54–2.68 (1H, m), 2.96 (1H, dt, J=12.8, 2.8 Hz), 3.14 (1H, d, J=13.3 Hz), 3.75 (1H, d, J=13.3 Hz), 4.23 (1H, s), 4.29–4.37 (1H, m), 4.53 (dt, J=3.2, 11.0 Hz), 7.20–7.56 (10H, m). MS (FAB): m/z 268 (M+H; 100%).

DESCRIPTION 17

4-Benzyl-2-(R)-(3,5-bis(trifluoromethyl) benzoyloxy)-3-(S)-phenylmorpholine

A solution of 2.67 g (10.0 mmol) of the compound of Description 16 in 40 ml of dry THF was cooled to −78° C.

The cold solution was treated with 12.5 ml of 1.0M L-Selectride® solution in THF, maintaining the internal reaction temperature below −70° C. The resulting solution was stirred cold for 45 minutes and the reaction was charged with 3.60 ml (20.0 mmol) of 3,5-bis(trifluoromethyl)benzoyl chloride. The resulting yellow mixture was stirred cold for 30 minutes and the reaction was quenched with 50 ml of saturated aqueous sodium bicarbonate solution. The quenched mixture was partitioned between 300 ml of ether and 50 ml of water and the layers were separated. The organic layer was dried over magnesium sulfate. The aqueous layer was extracted with 300 ml of ether; the extract was dried and combined with the original organic layer. The combined organics were concentrated in vacuo. Flash chromatography on 150 g of silica gel using 37:3 v/v hexanes/ether as the eluant afforded 4.06 g (80%) of the title compound as a solid. $^1$H NMR (200 MHz, CDCl$_3$) δ2.50 (1H, dt, J=3.4, 12.0 Hz), 2.97 (1H, app d, J=12.0 Hz), 2.99 (1H, d, J=13.6 Hz), 3.72–3.79 (1H, m), 3.82 (1H, d, J=2.6 Hz), 4.00 (1H, d, J=13.6 Hz), 4.20 (dt, J=2.4, 11.6 Hz), 6.22 (1H, d, J=2.6 Hz), 7.22–7.37 (7H, m), 7.57 (2H, app d, J=6.8 Hz), 8.07 (1H, s), 8.47 (2H, s).

Analysis Calcd. for C$_{26}$H$_{21}$F$_6$NO$_3$: C, 61.29; H, 4.16; N, 2.75; F, 22.38; Found: C, 61.18; H, 4.14; N, 2.70; F, 22.13%.

DESCRIPTION 18

4-Benzyl-2-(R)-(1-(3,5-bis(trifluoromethyl)phenyl)ethenyloxy)-3-(S)-phenylmorpholine A solution of 2.50 g (4.9 mmol) of the compound of Description 17 and 2.50 g (12.0 mmol) of dimethyl titanocene (Description 4a), in 35 ml of 1:1 v/v THF/toluene was stirred in an oil bath at 80° C. for 16 hours. The reaction mixture was cooled and concentrated in vacuo. Flash chromatography on 150 g of silica gel using 3:1 v/v hexanes/methylene chloride as the eluant afforded 1.71 g (69%) of the title compound as a solid. $^1$H NMR (400 MHz, CDCl$_3$) δ2.42 (1H, dt, J=3.6, 12.0 Hz), 2.89 (app d, J=11.6 Hz), 2.92 (1H, d, J=13.6 Hz), 3.61–3.66 (1H, m), 3.73 (1H, d, J=2.8 Hz), 4.00 (1H, d, J=13.6 Hz), 4.09 (1H, dt, J=2.4, 11.6 Hz), 4.75 (1H, d, J=2.8 Hz), 4.79 (1H, d, J=2.8 Hz), 5.36 (1H, d, J=2.4 Hz), 7.23–7.41 (7H, m), 7.63 (1H, app d, J=7.2 Hz), 7.79 (1H, s), 7.91 (2H, s). MS (FAB) m/z 508 (M+1, 25%).

Analysis Calcd. for C$_{27}$H$_{23}$F$_6$NO$_2$; C, 63.90; H, 4.57; N, 2.76; F, 22.46; Found: C, 63.71; H, 4.53; N, 2.68; F, 22.66%.

DESCRIPTION 19

2-(R)-(1-(R)-(3,5-Bis(trifluoromethyl)phenyl)ethoxy)-3-(S)-phenylmorpholine

A mixture of the compound of Description 18 (1.5 g) and 10% palladium on carbon catalyst (750 mg) in a mixture of isopropanol/ethyl acetate (25 ml, 3:2 v/v) was stirred under an atmosphere of hydrogen for 48 h. The catalyst was removed by filtration through celite and the reaction flask and filter pad were rinsed with ethyl acetate (500 ml). The filtrate was concentrated in vacuo, flash chromatography afforded epimer A (106 mg) and epimer B (899 mg) as clear oils. The title compound, epimer B had the following analysis:

$^1$H NMR (CDCl$_3$, 400 MHz) δ1.46 (3H, d, J=6.8 Hz), 1.92 (1H, br s), 3.13 (1H, dd, J=3.0, 12.6 Hz), 3.24 (1H, dt, J=3.6, 12.6 Hz), 3.62 (1H, dd, J=3.6, 11.2 Hz), 4.04 (1H, d, J=2.4 Hz), 4.14 (1H, dt, J=3.0, 11.2 Hz), 4.48 (1H, d, J=2.4 Hz), 4.90 (1H, q, J=6.8 Hz), 7.21–7.32 (7H, m), 7.64 (1H, s). MS (CI$^+$) m/z 420 (M$^+$+1, 20%), 178 (100%).

Analysis Calcd. for C$_{20}$H$_{19}$F$_6$NO$_2$: C, 57.28; H, 4.57; N, 3.34; F, 27.18; Found: C, 57.41; H, 4.61; N, 3.29; F, 27.23%.

DESCRIPTION 20

2-(R)-(1-(R)-(3,5-Bis(trifluoromethyl)phenyl)ethoxy)-4-(4-chlorobut-2-yn-yl)-3-(S)-phenylmorpholine The compound of Description 19 was reacted with 1,4-dichlorobut-2-yne following the procedure illustrated in Description 6 to afford the title compound. $^1$H NMR (250 MHz, CDCl$_3$) δ1.48 (3H, d, J=6.5 Hz), 2.85–3.00 (2H, m), 3.33 (2H, br s), 3.60 (1H, d, J=2.8 Hz), 3.72 (1H, br dt), 4.14 (2H, t, J=1.75 Hz), 4.31–4.41 (2H, m), 4.87 (1H, q, J=6.5 Hz), 7.17 (2H, s), 7.30–7.35 (3H, m), 7.37 (2H, m), 7.61 (1H, s).

DESCRIPTION 21

4-Benzyl-2-(R)-(1-(S)-(3,5-bis(trifluoromethyl)phenyl)-2-hydroxyethoxy)-3-(S)-(4-fluorophenyl)morpholine The compound of Description 4 (12.8 g) was dissolved in tetrahydrofuran (50 ml) and the mixture was cooled in ice. Borane (49 ml of 1.0M in tetrahydrofuran) was added dropwise and the reaction mixture was stirred at room temperature for 3 hr. The solution was cooled in ice and sodium hydroxide (120 ml, 1M) and hydrogen peroxide (36 ml, 30 wt. %) were added dropwise cautiously. The resulting mixture was stirred for 1 h, then diluted with water (200 ml) and extracted with ethyl acetate (3×50 ml). The organic extracts were washed with sodium sulfite and then brine. The organic phase was dried (MgSO$_4$) and evaporated to give a clear oil. Plc (50:50 ethyl acetate/hexane) indicated two main products which were separated by flash chromatography on silica using a gradient elution of 1–30% ethyl acetate in hexane. The minor product eluted first (2.3 g) and the major product eluted last (8 g). The major product was isolated as a white foam. $^1$H NMR (360 MHz, DMSO-d$_6$) δ2.23–2.29 (1H, m), 2.73 (1H, d), 2.80 (1H, d, J=13.0 Hz), 3.48 (1H, d, J=3.5 Hz), 3.45–3.52 (2H, m), 3.56–3.65 (2H, m), 4.00–4.06 (1H, m), 4.37 (1H, d, J=3.0 Hz), 4.81 (1H, t, J=6.0 Hz), 4.92 (1H, t, J=5.5 Hz), 7.14 (2H, t, J=9.0 Hz), 7.23–7.33 (5H, m), 7.35 (2H, s), 7.57 (2H, t), 7.85 (1H, s). MS (CI+) m/z 544 (M$^+$+1, 100%).

DESCRIPTION 22

2-(R)-(1-(S)-(3,5-bis(trifluoromethyl)phenyl)-2-hydroxyethoxy)-3-(S)-(4-fluorophenyl)morpholine The compound of Description 21 (8 g) as dissolved in ethyl acetate (100 ml) and isopropanol (50 ml) and palladium on charcoal (1.5 g) was added to the solution. This mixture was hydrogenated at 40 psi overnight. The catalyst was removed by filtration and the solvents were removed in vacuo. The residue was purified by flash silica chromatography using 1–10% methanol in dichloromethane as eluant. This afforded the product as a white powder (5.7 g, 90%). $^1$H NMR (360 MHz, CDCl$_3$) δ2.68–2.73 (1H, m), 3.03–3.15 (1H, m), 3.43–3.65 (3H, m), 3.95 (1H, d, J=3.0 Hz), 4.1$_{2-4}$22 (1H, m), 4.40 (1H, d, J=3.0 Hz), 4.89 (1H, t, J=7.0 Hz), 6.99 (t, J=9.0 Hz), 7.15 (2H, s), 7.26–7.31 (1H, m), 7.62 (1H, s). MS (CI+) m/z 454 (M$^+$+1, 100%).

DESCRIPTION 23

3-(S)-(4-Fluorophenyl)-2-(R)-(1-(S)-(3-fluoro-5-(trifluoromethyl)phenyl)-2-hydroxyethoxy)morpholine Step A: 4-Benzyl-3-(S)-(4-fluorophenyl)-2-(R)-(1-(S)-(3-fluoro-5-(trifluoromethyl)phenyl1)-2-hydroxyethoxy)morpholine The compound of Description 9 (0.8 g) was dissolved in tetrahydrofuran (5 ml) at room temperature and borane (5 ml, 1.0M in tetrahydrofuran) was added. The solution was stirred under nitrogen for 30 min until all starting material had reacted. Hydrogen peroxide (5 ml, 29% aq.) and sodium hydroxide (10 ml, 4N) were added dropwise to the cooled (0° C.) solution with much effervescence. The resulting mixture was extracted with ethyl acetate, the organic phase was washed with sodium bisulfite and brine, dried ($MgSO_4$) and evaporated to afford a colourless oil (1 g). This material was not purified further but reacted as described in the following step.

Step B: 3-(S)-(4-Fluorophenyl)-2-(R)-(1-(S)-(3-fluoro-5-(trifluoromethyl) phenyl)-2-hydroxyethoxy)morpholine The compound of (a) above (1 g) was dissolved in ethyl acetate/2-propanol (20 ml, 3:1) and treated with Pd on carbon (100 mg). The mixture was hydrogenated at 60 psi for 12 h. The catalyst was removed by filtration and the solvent was removed in vacuo. The residue was purified by medium pressure chromatography on silica (Lobar) using 5% methanol in dichloromethane as eluant. The product was recrystallised from ether.

$^1$H NMR (360 MHz, DMSO-$d_6$) δ2.77–3.04 (3H, m), 3.36–3.51 (2H, m), 3.93 (1H, br s), 4.05–4.13 (1H, m), 4.36 (1H, d, J=2.0 Hz), 4.72 (1H, t, J=5.0 Hz), 4.98 (1H, t, J=7.0 Hz), 6.66 (1H, d, J=9.2 Hz), 6.89 (1H, s), 7.10 (2H, t, J=9.0 Hz), 7.33–7.37 (2H, m), 7.41 (1H, d, J=9.0 Hz); MS (CI+) m/z 404 (M$^+$+1, 100).

DESCRIPTION 24

4-(4-(Chlorobut-2-yn-yl)-3-(S)-(4-fluorophenyl)-2-(R)-(1-(S)-(3-fluoro-5-(trifluoromethyl)phenyl)-2-hydroxyethoxy)morpholine The compound of Description 23 was reacted with 1,4-dichlorobut-2-yne following the procedure illustrated in Description 6 to afford the title compound. $^1$H NMR (250 MHz,CDCl$_3$) δ2.88–3.00 (3H, m), 3.31 (2H, m), 3.64–3.76 (4H, m), 4.15 (1H, m), 4.32–4.43 (2H, m), 4.79 (1H, m), 6.43 (1H, b d, J=9.1 Hz), 6.79 (1H, s), 7.03–7.13 (3H, m), 7.38 (2H, m), MS (ES$^{30}$) m/z=490.

DESCRIPTION 25

2-(R)-(1-(S)-(3,5-Bis(trifluoromethyl)phenyl)-2-tert-butyldimethylsilyloxyethoxy)-3-(S)-(4-fluorophenyl)morpholine The product from Description 22 (2 g) was dissolved in anhydrous dichloromethane (16 ml), under nitrogen, and cooled to 0° C. 2,6-Lutidine (0.5 ml) and tert-butyldimethyltrifluoromethane sulfonate (1.0 ml) were then added and the mixture stirred for 15 mins. The reaction mixture was washed (H20, brine), dried (MgSO$_4$) and evaporated in vacuo. Purification by gravity silica column using 20%–50% ethylacetate/petrol as eluant afforded the title compound as a colourless oil. $^1$H NMR (250 MHz, CDCl$_3$) δ−0.04 (3H, s), 0.00 (3H, s), 0.87 (9H, s), 3.15–3.36 (2H, m), 3.64–370 (2H, m), 3.90–3.96 (1H, m), 4.10 (1H, d, J=2.2 Hz), 4.22–4.53 (1H, m), 4.53 (1H, d, J=2.2 Hz), 4.91 (1H, t, J=5.9 Hz), 7.04–7.14 (2H, m), 7.29–7.36 (4H, m), 7.74 (1H, br s). MS (ES$^+$) m/z=567.

DESCRIPTION 26

2-(R)-(1-(S)-(3,5-Bis(trifluoromethyl)phenyl)-2-tert-butyldimethylsilyloxyethoxy)-3-(S)-(4-fluorophenyl)-4-(4-chlorobut-2-ynyl)morpholine The compound of Description 25 and 1,4-dichlorobut-2-yne was reacted following the procedure illustrated in Description 6 to afford the title compound as a clear oil. $^1$H NMR (360 MHz, CDCl$_3$) δ0.00 (3H, s), 0.04 (3H, s), 0.91 (9H, s), 2.95–3.09 (2H, m), 3.40 (2H, br s), 3.72–3.83 (3H, m), 4.01 (1H, dd, J=10.2, 5.5 Hz), 4.25 (2H, m), 4.50 (2H, m), 4.9 (1H, t, J=5.9 Hz), 7.15 (2H, t, J=8.7 Hz), 7.29 (2H, s), 7.52 (2H, br s), 7.76 (1H, s).

DESCRIPTION 27

4-Benzyl-2-(R)-(3-fluoro-5-(trifluoromethyl)benzoyloxy)-3-(S)-phenylmorpholine

The title compound was prepared in an analogous fashion to Description 17 using the product from Description 16 and 3-fluoro-5-(trifluoromethyl)benzoyl chloride. $^1$H NMR (250 MHz,CDCl$_3$) δ2.47 (1H, dt, J=3.4, 12.0 Hz), 2.93 (1H, s), 2.98 (1H, s), 3.72–3.80 (2H, m), 3.98 (1H, d, J=13.5 Hz), 4.11–4.24 (1H, m), 7.22–7.36 (8H, m), 7.56 (3H, m), 7.89 (1H, d, J=8.0 Hz), 8.10 (1H, s).

DESCRIPTION 28

4-Benzyl-2-(R)-(1-(3-fluoro-5-(trifluoromethyl)phenyl)ethenyloxy)-3-(S)-phenylmorpholine The title compound was prepared as a colourless oil in an analogous fashion to Description 18 using the product from Description 27. $^1$H NMR (250 MHz,CDCl$_3$) δ2.41 (1H, dt, J=3.6, 12.0 Hz), 2.87–2.94 (2H, m), 3.62 (1H, m), 3.72 (1H, d, J=2.8 Hz), 3.97–4.17 (2H, m), 7.23–7.43 (10 H, m), 7.54 (1H, s), 7.63 (2H, m).

DESCRIPTION 29

2-(R)-(1-(R)-(3-Fluoro-5-(trifluoromethyl)phenyl)ethoxy)-3-(S)-phenylmorpholine

The title compound was prepared in an analogous fashion to Description 19 using the product from Description 28. $^1$H NMR (250 MHz,CDCl$_3$) δ1.33 (3H, d, J=6.6 Hz), 1.93 (1H, br s), 3.02–3.22 (2H, m), 3.53 (1H, m), 3.96 (1H, d, J=2.4 Hz), 4.00–4.11 (1H, m), 4.38 (1H, d, J=2.4 Hz), 4.75 (1H, m), 6.24 (1H, d, J=9.2 Hz), 6.80 (1H, s), 6.98 (1H, d, J=8.3 Hz), 7.13–7.31 (5H, m). MS (ES$^+$) m/z 369.

DESCRIPTION 30

4-(4-Chlorobut-2-yn-yl)-2-(R)-(1-(R)-(3-fluoro-5-(trifluoromethyl)phenyl)ethoxy)-3-(S)-phenylmorpholine The title compound was prepared in an analogous fashion to Description 20 using the product from Description 29. $^1$H NMR (250 MHz,CDCl$_3$) δ1.43 (3H, d, J=6.6 Hz), 2.86–2.99 (2H, m), 3.37 (2H, s), 3.61 (1H, d, J=2.6 Hz), 3.68–3.73 (1H, m), 4.08–4.18 (2H, m), 4.30–4.41 (2H, m), 4.74–4.82 (1H, m), 6.26 (1H, d, J=9.09 Hz), 6.84 (1H, s), 7.02 (2H, d, J=8.4 Hz), 7.35 (5H, br s).

EXAMPLE 1

2-(R)-(1-(R)-(3,5-Bis(trifluoromethyl)phenyl)ethoxy)-3-(S)-(4-fluorophenyl)-4-(4-morpholinobut-2-yn-yl)morpholine The compound of Description 6 (0.5 g), potassium carbonate (0.4 g) and morpholine (0.1 g) were stirred in dry dimethylformamide under nitrogen for 5 h. The mixture was partitioned between ethyl acetate and water, the organic phase was washed with brine, dried (MgSO$_4$) and evaporated in vacuo. The residue was purified on silica using ethyl acetate in petrol (1:1) followed by ethyl acetate (100%) as eluent. This afforded the title compound as a clear oil. $^1$H NMR (250 MHz, CDCl$_3$) δ1.48 (3H, d, J=6.6 Hz), 2.52 (4H, m), 2.83–3.01 (2H, m), 3.29 (4H, s), 3.59 (1H, d, J=2.77 Hz), 3.69–3.75 (5H, m), 4.29–4.39 (2H, m), 4.88 (1H, q, J=6.5 Hz), 7.0 (2H, t, J=8.7 Hz), 7.17 (2H, s), 7.36 (2H, br s), 7.63 (1H, s).

M/S (ES$^+$) m/z 575 (MH$^+$, 100%).

EXAMPLE 2

2-R)-(1-(R)-(3,5-Bis(trifluoromethyl)phenyl)ethoxy)
-4-(4-(N,N-dimethylamino)but-2-yn-yl)-3-(S)-(4-fluorophenyl)morpholine This compound was prepared from the reaction of the compound of Description-6 and dimethylamine according to the procedure described in Example 1. $^1$H NMR (250 MHz, CDCl$_3$) δ1.48 (3H, d, J=6.6 Hz), 2.27 (6H, s), 2.84 (1H, br d), 2.98 (1H, dd, J=3.6, 11.8 Hz), 3.29 (4H, m), 3.63 (1H, d, J=2.8 Hz), 3.71 (1H, m), 4.34 (2H, m), 4.88 (1H, q, J=6.6 Hz), 7.02 (2H, t, J=8.7 Hz), 7.17 (2H, s), 7.37 (2H, br s), 7.63 (1H, s). MS (ES$^+$) m/z 533 (MH$^+$, 100%).

EXAMPLE 3

4-(4-Azetidinylbut-2-yn-yl)-2-(R)-(1-(R)-(3,5-bis(trifluoromethyl)phenyl)ethoxy)-3-(S)-(4-fluorophenyl)morpholine This compound was prepared from the reaction of the compound of Description 6 and azetidine according to the procedure described in Example 1. $^1$H NMR (250 MHz, CDCl$_3$) δ1.47 (3H, d, J=6.6 Hz), 1.99–2.10 (2H, m), 2.82–2.86 (1H, m), 2.99 (1H, dd, J=3.7, 11.9 Hz), 3.21–3.32 (8H, m), 3.64 (1H, d, J=2.79 Hz), 3.71 (1H, m), 4.29–4.40 (2H, m), 4.88 (1H, q, J=6.6 Hz), 7.02 (2H, t, J=8.7 Hz), 7.17 (2H, s), 7.38 (2H, br s). 7.63 (1H, s).

EXAMPLE 4

2-(R)-(1-(R)-(3,5-Bis(trifluoromethyl)phenyl)ethoxy)-3-(S-(4-fluorophenyl)-4-(4-(imidazolyl)but-2-yn-yl)morpholine The compound of Description 6 was added to a solution of imidazole (77 mg) and sodium hydride (42 mg, 60% in oil) in dry dimethylformamide. The mixture was allowed to stir for 16 h and then was partitioned between water and ethyl acetate. The organic layer was washed with water, brine and dried (MgSO$_4$) and evaporated in vacuo. The compound was purified on silica using dichloromethane (100%) as eluent and gradient elution to dichloromethane/methanol/ammonia (97:2:1). This afforded the title compound as a colourless oil. $^1$H NMR (250 MHz, CDCl$_3$) δ1.48 (3H, d, J=6.6 Hz), 2.86–2.91 (3H, m), 3.30 (2H, s), 3.51 (1H, d, J=2.8 Hz), 3.68–3.74 (1H, m), 4.28–4.39 (2H, m), 4.87 (1H, q, J=6.5 Hz), 6.99–7.09 (4H, m), 7.16 (2H, s), 7.27 (1H, br s), 7.57 (1H, s), 7.63 (1H, s). MS (ES$^+$) m/z 556 (MH$^+$, 100%).

EXAMPLE 5

2-(R)-(-(R)-(3,5-Bis(trifluoromethyl)phenyl)ethoxy)-3-(S)-(4-fluorophenyl)-4-(4-(N-methylpiperazinyl)but-2-yn-yl)morpholine This compound was prepared from the reaction of the compound of Description 6 and N-methylpiperazine according to the procedure described in Example 1. $^1$H NMR (250 MHz, CDCl$_3$) δ1.47 (3H, d, J=6.6 Hz), 1.9–1.95 (2H, m), 2.30 (3H, s), 2.4–2.6 (6H, m), 2.83–2.86 (1H, m), 2.93 (1H, dt, J=12.0, 3.6 Hz), 3.21–3.29 (4H, m), 3.59 (1H, d, J=3.0 Hz), 3.70 (1H, d, J=12.0 Hz), 4.33 (2H, q, J=12.6 Hz), 4.87 (1H, q, J=6.6 Hz), 7.00 (2H, t, J=7.2 Hz), 7.17 (2H, s), 7.36 (2H, br m), 7.62 (1H, s).

EXAMPLE 6

4-(4-Bis(methoxyethyl)aminobut-2-yn-yl)-2-(R)-(1-(R)-(3,5-bis(trifluorometbyl)phenyl)ethoxy)-3-(S)-(4-fluorophenyl)morpholine The compound of Description 6 was reacted with bis (methoxyethyl)amine according to the procedure described in Example 1 to afford the title compound as a clear oil. $^1$H NMR (360 MHz, CDCl$_3$) δ1.48 (3H, d, J=6.8 Hz), 2.74 (4H, br m), 2.84 (1H, br d, J=12 Hz), 2.95 (1H, dt, J=12.3 Hz), 3.29 (2H, br s), 3.33 (6H, s), 3.49 (6H, m), 3.61 (1H, d, J=3 Hz), 3.70 (1H, br d), 4.33 (2H, app. q), 4.87 (1H, q, J=6.8 Hz), 7.01 (2H, t, J=8.5 Hz), 7.17 (2H, s), 7.36 (2H, m), 7.63 (1H, s). MS (ES) m/z 621 (M$^+$+, 100%).

EXAMPLE 7

2-(R)-(1-(R)-(3,5-Bis(trifluoromethyl)phenyl)ethoxy)-3-(S)-(4-fluorophenyl)-4-(4-pyrrolidinobut-2-yn-yl)morpholine The compound of Description 7 (0.85 g), paraformaldehyde (66 mg), pyrrolidine (0.18 ml) and copper (I)chloride (8 mg) in dioxane were heated at 80° C. for 4 h (J. Med. Chem. 1985, 28, 1760). The mixture was cooled and concentrated in vacuo. The residue was purified by chromatography on silica using ethyl acetate in hexane (1:4→100%) followed by 10% methanol in ethyl acetate as eluant. This afforded the product as a viscous oil (870 mg, 87%). $^1$H NMR (360 MHz, CDCl$_3$) δ1.47 (3H, d, J=6.6 Hz), 1.80 (4H, m), 2.59 (4H, br s), 2.83 (1H, d, J=11.1 Hz), 2.95 (1H, ddd, J=3.6, 11.9, 11.9 Hz), 3.28 (2H, s), 3.41 (2H, s), 3.61 (1H, d, J=2.7 Hz), 3.71 (1H, dd, J=2.2, 11.1Hz), 4.32 (2H, m), 4.87 (1H, q, J=6.6 Hz), 7.01 (2H, t, J=8.6 Hz), 7.17 (2H, s), 7.36 (2H, br s), 7.63 (1H, s). IR (film) v–2810 (m), 1741 (w), 1608 (m), 1510 (s), 1280 (s), 1060 (s), 900 (s), 685 (s) cm$^{-1}$ MS (CI+) m/z 559 (ME, 100%).

EXAMPLE 8

3-(S)-(4-Fluorophenyl)-2-(R)-(1-(R)-(3-fluoro-5-(trifluoromethyl)phenyl) ethoxy)-4-(4-morpholinobut-2-ynyl)morpholine The compound of Description 11 was reacted with morpholine according to the procedure described in Example 1. $^1$H NMR (360 MHz, CDCl$_3$) δ1.43 (3H, d, J=6.6 Hz), 2.53 (4H, t, J=4.4 Hz), 2.85 (1H, br d, J=10.5 Hz), 2.94 (1H, dt, J=11.7, 3.5 Hz), 3.31 (4H, d, J=5.5 Hz), 3.60 (1H, d, J=2.8 Hz), 3.66–3.76 (5H, m), 4.33 (2H, dt, J=13.3, 2.8 Hz), 4.77 (1H, q, J=6.6 Hz), 6.37 (1H, d, J=9.1 Hz), 6.81 (1H, s), 7.00–7.07 (3H, m), 7.35 (2H, br s). MS (CI+) m/z 525 (M+1, 98%), 524 (M+, 100).

EXAMPLE 9

3-(S)-(4-Fluorophenyl)-4-(4-morpholinobut-2-ynyl)-2-(R)-(1-(3-(trifluoromethyl)phenyl)ethoxy)morpholine The compound of Description 15 was reacted with morpholine according to the procedure described in Example 1.

¹H NMR (360 MHz, CDCl₃) δ1.44 (3H, d, J=6.6 Hz), 2.52 (4H, t, J=4.6 Hz), 2.84 (1H, br d, J=11.6 Hz), 2.94 (1H, dt, J=11.9, 3.5 Hz), 3.30 (4H, dd, J=3.6, 1.4 Hz), 3.58 (1H, d, J=2.8 Hz), 3.66–3.75 (5H, m), 4.35 (1H, dt, J=11.7, 2.9 Hz), 4.78 (1H, q, J=6.6 Hz), 6.80 (1H, d, J=7.7 Hz), 6.96–7.04 (3H, m), 7.15 (1H, t, J=7.7 Hz), 7.35 (3H, br d, J=7.5 Hz). MS (CI+) m/z 507 (M+1, 100%).

EXAMPLE 10

4-(4-Azetidinylbut-2-ynyl)-3-(S)-(4-fluorophenyl)-2-(R)-(1-(3-(trifluoromethyl)phenyl)ethoxy)morpholine The compound of Description 15 was reacted with azetidine according to the procedure described in Example 1. ¹H NMR (360 MHz, CDCl₃) δ1.44 (3H, d, J=6.6 Hz), 2.04 (2H, quin, J=7.1 Hz), 2.84 (1H, br d, J=11.8 Hz), 2.98 (1H, dt, J=11.9, 3.6 Hz), 3.02–3.32 (8H, m), 3.62 (1H, d, J=2.8 Hz), 3.69 (1H, m), 4.33 (1H, d, J=2.8 Hz), 4.36 (1H, dt, J=11.8, 2.7 Hz), 4.79 (1H, q, J=6.5 Hz), 6.80 (1H, d, J=7.6 Hz), 6.96–7.04 (3H, m) 7.15 (1H, t, J=7.7 Hz), 7.35 (3H, br d, J=7.7 Hz). MS (CI+) m/z 477 (M+1, 100%).

EXAMPLE 11

2-(R)-(1-(R)-(3,5-Bis(trifluoromethyl)phenyl)ethoxy)-4-(4-(N-(2-methoxyethyl)-N-methylamino)but-2-yn-yl)-3-(S)-phenylmorpholine The compound of Description 20 was reacted with N-(2-methoxyethyl)-N-methylamine according to the procedure described in Example 1 to afford the title compound. ¹H NMR (250 MHz, CDCl₃) δ1.48 (3H, d, J=6.5 Hz), 2.33 (3H, s), 2.62 (2H, t, J=5.5 Hz), 2.84 (1H, br d), 2.98 (1H, dt, J=3.5, 12.0 Hz), 3.33–3.34 (2H, m), 3.35 (3H, s), 3.41 (2H br s), 3.46 (2H, t, J=5.5 Hz), 3.63 (1H, d, J=2.8 Hz), 3.72 (1H, br d), 4.3₁.₄.41 (2H, m), 4.86 (1H, q, J=6.5 Hz), 7.16 (2H, s), 7.31–7.36 (3H, m), 7.36 (2H, m), 7.60 (1H, s).

EXAMPLE 12

2-(R)-(1-(R)-(3,5-Bis(trifluoromethyl)phenyl)ethoxy)-4-(4-(N-cyclopropyl-N-(2-methoxyethyl)amino)but-2-yn-yl)-3-(S)-phenylmorpholine The compound of Description 20 was reacted with N-cyclopropyl-N-(2-methoxyethyl)amine according to the procedure described in Example 1 to afford the title compound. ¹H NMR (360 MHz, CDCl₃) δ0.47–0.49 (4H, m), 1.48 (3H, d, J=6.5 Hz), 1.94 (1H, br quin), 2.85–2.88 (3H, m), 2.98 (1H, dt, J=3.6, 12.0 Hz), 3.33 (3H, s), 3.33–3.35 (2H, m), 3.47–3.52 (4H, m), 3.63 (1H, d, J=2.8 Hz), 3.71 (1H, dd, J=2.0, 11.0 Hz), 4.32–4.40 (2H, m), 4.86 (1H, q, J=6.5 Hz), 7.16 (2H, s), 7.30–7.31 (3H, m), 7.37 (2H, m), 7.60 (1H, s).

EXAMPLE 13

2-(R)-(1-(R)-(3,5-Bis(trifluoromethyl)phenyl)ethoxy)-4-(4-(N-isopropyl)-N-(2-methoxyethyl)amino)but-2-yn-yl)-3-(S)-phenylmorpholine The compound of Description 20 was reacted with N-isopropyl-N-(2-methoxyethyl)amine according to the procedure described in Example 1 to afford the title compound. ¹H NMR (360 MHz, CDCl₃) δ1.06 (6H, d, J=6.0 Hz), 1.47 (3H, d, J=6.5 Hz), 2.72 (2H, t, J=6.0 Hz), 2.82–3.00 (3H, m), 3.30–3.33 (2H, m), 3.33 (3H, s), 3.41–3.47 (4H, m), 3.61 (1H, d, J=2.5 Hz), 3.71 (1H, br d), 4.32–4.39 (2H, m), 4.86 (1H, q, J=6.5 Hz), 7.16 (2H, s), 7.27–7.31 (3H, m), 7.36 (2H, br s), 7.60 (1H, s).

EXAMPLE 14

4-(4-(N,N-Dimethylamino)but-2-yn-yl)-3-(S)-(4-fluorophenyl)-2-(R)-(1-(S)-(3-fluoro-5-(trifluoromethyl)phenyl-2-hydroxyethoxy)morpholine The compound of Description 24 was reacted with dimethylamine according to the procedure described in Example 1 to afford the title compound as a clear oil. ¹H NMR (360 MHz,CDCl₃) δ2.28 (6H, s), 2.88–2.97 (2H, m), 3.24 (2H, s), 3.30 (2H, d, J=9.9 Hz), 3.62 (3H, m), 3.72 (1H, m), 4.35–4.23 (2H, m), 4.79 (1H, m), 6.42 (1H, d, J=8.6 Hz), 6.79 (1H, s), 7.04–7.12 (3H, m), 7.38 (2H, vbr s). M/Z (ES⁺) m/z=498.

EXAMPLE 15

4-(4-Azetidinylbut-2yn-yl)-3-(S)-(4-fluorophenyl)-2-R)-(1-(S)-(3-fluoro-5-(trifluoromethyl)phenyl)-2-hydroxyethoxy)morpholine The title compound was prepared from the reaction of the compound of Description 24 and azetidine according to the procedure described in Example 1. ¹H NMR (360 MHz, CDCl₃) δ2.04 (2H, m), 2.40 (1H, vb s), 2.88–2.97 (3H, m), 3.21–3.36 (7H,m), 3.57–3.74 (4H, m), 4.35–4.42 (2H, m), 4.77–4.81 (1H, m), 6.42 (1H, d, J=8.8 Hz), 6.77 (1H, s), 7.04–7.12 (3H, m), 7.38 (2H, vbr s).

EXAMPLE 16

2-(R)-(I-(S)-(3,5-Bis(trifluoromethyl)phenyl)-2-hydroxyethoxy)-4-(4-(N,N-dimethylamino)but-2-yn-yl)-3-(S)-(4-fluorophenyl)morpholine The title compound was prepared from the reaction of the compound of Description 26 and dimethylamine according to the procedure described in Example 1. Deprotection was effected by stirring with tetrabutylammonium fluoride (1.0M) in tetrahydrofuran for 60 minutes. The mixture was partitioned between ammonium chloride solution and ethyl acetate, and the organic layer washed (H₂O, brine), dried (MgSO₄) and evaporated in vacuo. The residue was purified on a gravity silica column using 5–10% methanol/ethyl acetate as eluant giving the title compound as an oil. ¹H NMR (360 MHz,CDCl₃) δ2.28 (6H, s), 2.88–2.98 (2H, m), 3.21–3.34 (4H, m), 3.64–3.75 (4H, m), 4.36–4.42 (2H, m), 4.86–4.90 (1H, m), 7.05 (2H, t, J=8.7 Hz), 7.17 (2H, s), 7.39 (2H, vbr s), 7.67 (1H, s). MS (ES⁺) 549 (M+H)⁺.

EXAMPLE 17

4-(4-Azetidinylbut-2-yn-yl)-2-(R)-(1-(S)-(3,5-bis(trifluoromethyl)phenyl)-2-hydroxyethoxy)-3-(S)-(4-fluorophenyl)morpholine The title compound was prepared from the reaction of the compound of Description 26 and azetidine according to the procedure described in Example 16, which gave a white foam. ¹H NMR (250 MHz,CDCl₃) δ2.05 (2H, m), 2.37 (1H, vbr s), 2.92 (2H, m), 3.18–3.29 (8H, m), 3.66–3.76 (4H, m), 4.35–4.47 (2H, m), 4.87–4.91 (1H, m), 7.06 (2H, t, J=8.7 Hz), 7.17 (2H, s), 7.41 (2H, br s), 7.67 (1H, s). M/S (ES⁺) m/z 560.

EXAMPLE 18

4-(4-N-Bis(2-methoxy)ethyl-N-methylamino)but-2-yn-yl)-2-(R)-(1-(R)-(3,5-bis(trifluoromethyl)phenyl)ethoxy)-3-(S)-(4-fluorophenyl)morpholine The compound of Description 6 was reacted with methylaminoacetaldehyde dimethyl acetal according to the procedure described in Example 1 to afford the title compound. ¹H NMR (250 MHz,CDCl₃) δ1.48 (3H, d, J=6.6 Hz), 2.36 (3H, s), 2.58 (2H, d, J=5.4 Hz), 2.81–3.03 (2H, m), 3.30 (2H, m), 3.36 (6H, s), 3.43 (2H, br s), 3.61 (1H, d, J=2.8 Hz), 3.68–3.74 (1H, m), 4.29–4.40 (2H, m), 4.49 (1H, t, J=5.4 Hz), 4.88 (1H, m), 7.02 (2H, t, J=8.7 Hz), 7.17 (2H, s), 7.37 (2H, vbr s), 7.63 (1H, s).

EXAMPLE 19

2-(R)-(1-(R)-(3,5-Bis(trifluoromethyl)phenyl) ethoxy)-3-(S)-(4-fluorophenyl)-4-(4-(2-(S)-(methoxymethyl)pyrrolidino)but-2-yn-yl) morpholine The compound of Description 6 was reacted with (S)(+)-2-(methoxymethyl)pyrrolidine according to the procedure described in Example 1 to afford the title compound. ¹H NMR (250 MHz,CDCl₃) δ1.48 (2H, d, J=6.6 Hz), 1.70–2.05 (4H, m), 2.83–2.97 (3H, m), 3.32 (4H, br s), 3.38 (3H, s), 3.45 (1H, m), 3.58 (1H, m), 3.70–3.83 (4H, m), 4.29–4.39 (3H, m), 4.87 (1H, m), 7.02 (2H, t, J=8.7 Hz), 7.16 (2H, s), 7.36 (2H, vbr s), 7.63 (1H, s).

EXAMPLE 20

4-(4-(7-Azabicyclo[2.2.1]heptano)but-2-yn-yl)-2-(R)-(1-(R)-(3,5-bis(trifluoromethyl)phenyl)ethoxy)-3-(S)-(4-fluorophenyl)morpholine The compound of Description 6 was reacted with 7-azabicyclo[2.2.1]heptane hydrochloride according to the procedure described in Example 1 to afford the title compound. ¹H NMR (250 MHz,CDCl₃) δ1.30 (4H, m), 1.48 (3H, d, J=6.6 Hz), 1.75 (4H, m), 2.83–3.03 (2H, m), 3.17 (2H, d, J=1.8 Hz), 3.27 (2H, d, J=1.3 Hz), 3.37 (2H, m), 3.62 (1H, d, J=2.8 Hz), 3.68–3.73 (1H, m), 4.28–4.39 (2H, m), 4.88 (1H, q, J=6.6 Hz), 7.01 (2H, t, 8.7 Hz), 7.17 (2H, s), 7.37 (2H, br s), 7.63 (1H, s).

EXAMPLE 21

2-(R)-(1-(R)-(3,5-Bis(trifluoromethyl)phenyl) ethoxy)-4-(4-diisopropylaminobut-2-yn-yl)-3-(S)-(4-fluorophenyl)morpholine The compound of Description 6 was reacted with N,N-diisopropylamine according to the procedure described in Example 1 to afford the title compound. ¹H NMR (360 MHz,CDCl₃) δ1.08 (12H, d, J=4.6 Hz), 1.47 (3H, d, J=4.6 Hz), 2.81 (1H, br d, J=7.5 Hz), 2.97 (1H, dt, J=2.6 Hz, 8.3 Hz), 3.16 (2H, m), 3.25 (2H, t, J=1.3 Hz), 3.41 (2H, t, J=1.3 Hz), 3.61 (1H, d, J=2.0 Hz), 3.70 (1H, m), 4.27–4.37 (2H, m), 4.87 (1H, q, J=4.6 Hz), 7.01 (2H, t, J=6.0 Hz), 7.17 (2H, s), 7.35 (2H, br s), 7.63 (1H, s).

EXAMPLE 22

2-(R)-(1-(R)-(3-Fluoro-5-(trifluoromethyl)phenyl) ethoxy)-4-(4-(2-(S)-(methoxymethyl)pyrrolidino) but-2-yn-yl)-3-(S)-phenylmorpholine The title compound was prepared from the reaction of the compound of Description 30 and 2-(S)-(methoxymethyl) pyrrolidine according to the procedure described in Example 1. ¹H NMR (250 MHz,CDCl₃) δ1.43 (3H, d, J=6.6 Hz), 1.90 (4H, m), 2.62 (1H, q, J=7.54 Hz), 2.78–2.86 (2H, m), 2.93–3.03 (2H, m), 3.27–3.41 (7H, m), 3.58 (2H, m), 3.64 (1H, d, J=2.84 Hz), 3.71 (1H, dd, J₁=1.8 Hz, J₂=2.18 Hz), 4.36 (1H, td, J₁=11.02 Hz, J₂=2.83 Hz), 4.78 (1H, q, J=6.57 Hz), 6.25 (1H, d, J=9.12 Hz), 6.84 (1H, s), 7.02 (1H, d, J=8.30 Hz), 7.34 (5H, s).

EXAMPLE 23

2-(R)-(1-(R)-(3,5-Bis(trifluoromethyl)phenyl) ethoxy)-3-(S)-(4-fluorophenyl)-4-(2-(2-(S)-hydroxymethyl)pyrrolidino)but-2-yn-yl) morpholine The title compound was prepared from the reaction of the compound of Description 6 and 2-(S)-(hydroxymethyl) pyrrolidine according to the procedure described in Example 1. ¹H NMR (250 MHz,CDCl₃) δ1.48 (3H, d, J=6.60 Hz), 1.71–1.90 (4H, m), 2.18 (2H, br s), 2.61–3.06 (5H, m), 3.29 (2H, s), 3.58 (2H, m), 3.64 (1H, d, J=2.83 Hz), 3.77 (1H, dd, J₁=11.18 Hz, J₂=2.18 Hz), 4.34 (2H, td, J₁=11.02 Hz, J₂=2.83 Hz), 4.88 (1H, q, J=6.60 Hz), 7.02 (2H, t, J=8.65 Hz), 7.27 (2H, s), 7.36 (2H, br s), 7.63 (1H, s). MS m/z (ES+) 589.

The following examples illustrate pharmaceutical compositions according to the invention.

| EXAMPLE 24A Tablets containing 1–25 mg of compound | | | |
|---|---|---|---|
| | Amount mg | | |
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium stearate | 0.5 | 0.5 | 0.5 |

| EXAMPLE 24B Tablets containing 26–100 mg of compound | | | |
|---|---|---|---|
| | Amount mg | | |
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium stearate | 0.5 | 0.5 | 0.5 |

The compound of formula (I), cellulose, lactose and a poriton of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

| EXAMPLE 25 Parenteral injection | |
|---|---|
| | Amount mg |
| Compound of formula (I) | 1 to 100 mg |
| Citric acid monohydrate | 0.75 mg |
| Sodium phosphate | 4.5 mg |
| Sodium chloride | 9 mg |
| Water for injection | to 10 ml |

The sodium phosphate, citric acid monohydrate and sodium chloride are dissolved in a portion of the water. The compound of formula (I) is dissolved or suspended in the solution and made up to volume.

| EXAMPLE 26 Topical formulation | |
|---|---|
| | Amount mg |
| Compound of formula (I) | 1–10 g |
| Emulsifying wax | 30 g |
| Liquid paraffin | 20 g |
| White soft paraffin | to 100 g |

The white soft paraffin is heated until molten. The liquid paraffin and emulsifying wax are incorporated and stirred until dissolved. The compound of formula (I) is added and stirring continued until dispersed. The mixture is then cooled until solid.

EXAMPLE 27A
(Surface-Active Agent) Injection Formulation
 Compound of formula (I) up to 10 mg/kg
 Tween 80™ up to 2.5%
  [in 5% aqueous mannitol (isotonic)]

The compound of formula (I) is dissolved directly in a solution of the commercially available Tween 80™, (polyoxyethylenesorbitan monooleate) and 5% aqueous mannitol (isotonic).

EXAMPLE 27B
(Emulsion) Injection Formulation
 Compound of formula (I) up to 30 mg/ml
 Intralipid™ (10–20%)

The compound of formula (I) is dissolved directly in the commercially available Intralipid™ (10 or 20%) to form an emulsion.

| Example 27C - Alternative (Emulsion) Injectable Formulation | |
|---|---|
| | Amount |
| Compound of formula (I) | 0.1–10 mg |
| Soybean oil | 100 mg |
| Egg phospholipid | 6 mg |
| Glycerol | 22 mg |
| Water for injection | to 1 ml |

All materials are sterilized and pyrogen free. The compound of formula (I) is dissolved in soybean oil. An emulsion is then formed by mixing this solution with the egg phospholipid, glycerol and water. The emulsion is then sealed in sterile vials.

We claim:

1. A compound of the formula (I):

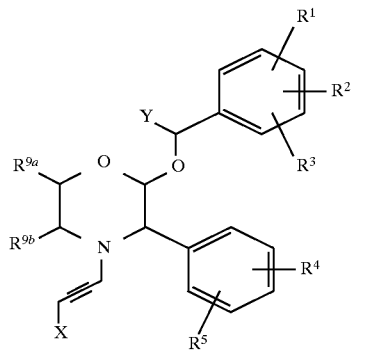

wherein
 X is a group of the formula $NR^6R^7$ or a C— or N-linked imidazolyl ring;
 Y is hydrogen or $C_{1-4}$alkyl optionally substituted by a hydroxy group;
 $R^1$ is hydrogen, halogen, $C_{1-6}$alkyl, $C_{1-6}$alkoxy, $CF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ each independently represent hydrogen or $C_{1-4}$alkyl;
 $R^2$ is hydrogen, halogen, $C_{1-6}$alkyl, $C_{1-6}$alkoxy substituted by $C_{1-4}$alkoxy or $CF_3$;
 $R^3$ is hydrogen, halogen or $CF_3$;
 $R^4$ is hydrogen, halogen, $C_{1-6}$alkyl, $C_{1-6}$alkoxy, hydroxy, $CF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ are as previously defined;
 $R^5$ is hydrogen, halogen, $C_{1-6}$alkyl, $C_{1-6}$alkoxy substituted by $C_{1-4}$alkoxy or $CF_3$;
 $R^6$ is hydrogen, $C_{1-6}$alkyl, $C_{3-7}$cycloalkyl, $C_{3-7}$cycloalkyl$C_{1-4}$alkyl, phenyl, or $C_{2-4}$alkyl substituted by $C_{1-4}$alkoxy or hydroxy;
 $R^7$ is hydrogen, $C_{1-6}$alkyl, $C_{3-7}$cycloalkyl, $C_{3-7}$cycloalkyl$C_{1-4}$alkyl, phenyl, or $C_{2-4}$alkyl substituted by one or two substituents selected from $C_{1-4}$alkoxy, hydroxy or a 4, 5 or 6 membered heteroaliphatic ring containing one or two heteroatoms selected from N, O and S;
 or $R^6$ and $R^7$, together with the nitrogen atom to which they are attached, form a saturated or partially saturated heterocyclic ring of 4 to 7 ring atoms, which ring may optionally contain in the ring one oxygen or sulphur atom or a group selected from $NR^8$, $S(O)$ or $S(O)_2$ and which ring may be optionally substituted by one or two groups selected from hydroxy$C_{1-4}$alkyl, $C_{1-4}$alkoxy$C_{1-4}$alkyl, oxo, $COR^a$ or $C_2R^a$ where $R^a$ is as previously defined;
 or $R^6$ and $R^7$ together with the nitrogen atom to which they are attached, form a non-aromatic azabicyclic ring system of 6 to 12 ring atoms;
 $R^8$ is hydrogen, $C_{1-4}$alkyl, hydroxy$C_{1-4}$alkyl or $C_{1-4}$alkoxy$C_{1-4}$alkyl; and
 $R^{9a}$ and $R^{9b}$ are each independently hydrogen or $C_{1-4}$alkyl, or $R^{9a}$ and $R^{9b}$ are joined so, together with the carbon atoms to which they are attached, there is formed a $C_{5-7}$ ring;
or a pharmaceutically acceptable salt thereof.

2. A compound as claimed in claim 1 wherein
 X is a group of the formula $NR^6R^7$ or a C— or N-linked imidazolyl ring;
 Y is hydrogen or $C_{1-4}$alkyl optionally substituted by a hydroxy group;
 $R^1$ is hydrogen, halogen, $C_{1-6}$alkyl, $C_{1-6}$alkoxy, $CF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ each independently represent hydrogen or $C_{1-4}$alkyl;
 $R^2$ is hydrogen, halogen, $C_{1-6}$alkyl, $C_{1-6}$alkoxy substituted by $C_{1-4}$alkoxy or $CF_3$;
 $R^3$ is hydrogen, halogen or $CF_3$;
 $R^4$ is hydrogen, halogen, $C_{1-6}$alkyl, $C_{1-6}$alkoxy, $CF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ are as previously defined;
 $R^5$ is hydrogen, halogen, $C_{1-6}$alkyl, $C_{1-6}$alkoxy substituted by $C_{1-4}$alkoxy or $CF_3$;

R⁶ is hydrogen, $C_{1-6}$alkyl, $C_{3-7}$cycloalkyl, $C_{3-7}$cycloalkyl$C_{1-4}$alkyl, phenyl, or $C_{2-4}$alkyl substituted by $C_{1-4}$alkoxy or hydroxy;

R⁷ is hydrogen, $C_{1-6}$alkyl, $C_{3-7}$cycloalkyl, $C_{3-7}$cycloalkyl$C_{1-4}$alkyl, phenyl, or $C_{2-4}$alkyl substituted by one or two substituents selected from $C_{1-4}$alkoxy, hydroxy or a 4, 5 or 6 membered heteroaliphatic ring containing one or two heteroatoms selected from N, O and S;

or R⁶ and R⁷, together with the nitrogen atom to which they are attached, form a saturated or partially saturated heterocyclic ring of 4 to 7 ring atoms, which ring may optionally contain in the ring one oxygen or sulphur atom or a group selected from NR⁸, S(O) or S(O)₂ and which ring may be optionally substituted by one or two groups selected from hydroxy$C_{1-4}$alkyl, $C_{1-4}$alkoxy$C_{1-4}$alkyl, oxo, COR$^a$ or CO₂R$^a$ where R$^a$ is as previously defined;

or R⁶ and R⁷ together with the nitrogen atom to which they are attached, form a non-aromatic azabicyclic ring system of 6 to 12 ring atoms;

R⁸ is hydrogen, $C_{1-4}$alkyl, hydroxy$C_{1-4}$alkyl or $C_{1-4}$alkoxy$C_{1-4}$alkyl; and R$^{9a}$ and R$^{9b}$ are each independently hydrogen or $C_{1-4}$alkyl, or R$^{9a}$ and R$^{9b}$ are joined so, together with the carbon atoms to which they are attached, there is formed a $C_{5-7}$ ring;

or a pharmaceutically acceptable salt thereof.

3. A compound as claimed in claim 1 wherein

X is a group of the formula NR⁶R⁷ or a C— or N-linked imidazolyl ring;

Y is hydrogen or $C_{1-4}$alkyl optionally substituted by a hydroxy group;

R¹ is hydrogen, halogen, $C_{1-6}$alkyl, $C_{1-6}$alkoxy, CF₃, NO₂, CN, CO₂R$^a$, CONR$^a$R$^b$, $C_{2-6}$alkenyl, $C_{2-6}$alkynyl or $C_{1-4}$alkyl substituted by $C_{1-4}$alkoxy, wherein R$^a$ and R$^b$ each independently represent hydrogen or $C_{1-4}$alkyl;

R² is hydrogen, halogen, $C_{1-6}$alkyl, $C_{1-6}$alkoxy substituted by $C_{1-4}$alkoxy or CF₃;

R³ is hydrogen, halogen or CF₃;

R⁴ is hydrogen, halogen, $C_{1-6}$alkyl, $C_{1-6}$alkoxy, CF₃, NO₂, CN, CO₂R$^a$, $C_{2-6}$alkenyl, $C_{2-6}$alkynyl or $C_{1-4}$alkyl substituted by $C_{1-4}$alkoxy, wherein R$^a$ and R$^b$ are as previously defined;

R⁵ is hydrogen, halogen, $C_{1-6}$alkyl, $C_{1-6}$alkoxy substituted by $C_{1-4}$alkoxy or CF₃;

R⁶ is hydrogen, $C_{1-6}$alkyl, $C_{3-7}$cycloalkyl, $C_{3-7}$cycloalkyl$C_{1-4}$alkyl, phenyl, or $C_{2-4}$alkyl substituted by $C_{1-4}$alkoxy or hydroxy;

R⁷ is hydrogen, $C_{1-6}$alkyl, $C_{3-7}$cycloalkyl, $C_{3-7}$cycloalkyl$C_{1-4}$alkyl, phenyl, or $C_{2-4}$alkyl substituted by $C_{1-4}$alkoxy or hydroxy;

or R⁶ and R⁷, together with the nitrogen atom to which they are attached, form a saturated or partially saturated heterocyclic ring of 4 to 7 ring atoms, and which ring may optionally contain in the ring one oxygen or sulphur atom or a group selected from NR⁸, S(O) or S(O)₂ and which ring may be optionally substituted by one or two groups selected from hydroxy$C_{1-4}$alkyl, $C_{1-4}$alkoxy$C_{1-4}$alkyl, oxo, COR$^a$ or CO₂R$^a$ where R$^a$ is as previously defined;

R⁸ is hydrogen, $C_{1-4}$alkyl, hydroxy$C_{1-4}$alkyl or $C_{1-4}$alkoxy$C_{1-4}$alkyl; and R$^{9a}$ and R$^{9b}$ are each independently hydrogen or $C_{1-4}$alkyl, or R$^{9a}$ and R$^{9b}$ are joined so, together with the carbon atoms to which they are attached, there is formed a $C_{5-7}$ ring;

or a pharmaceutically acceptable salt thereof.

4. A compound as claimed in claim 1 of formula (Ia):

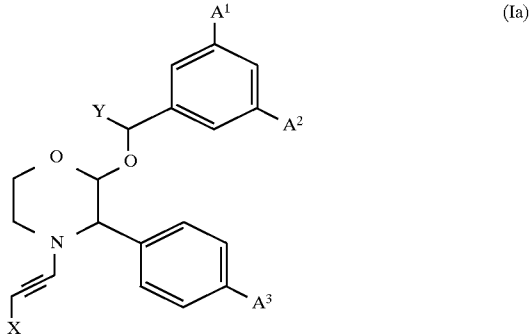

(Ia)

wherein

A¹ is fluorine or CF₃;

A² is fluorine or CF₃;

A³ is fluorine or hydrogen; and

X and Y are as defined in relation to formula (I);

or a pharmaceutically acceptable salt thereof.

5. A compound as claimed in claim 1 formula (Ib):

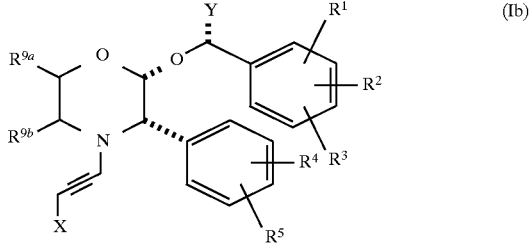

(Ib)

wherein R¹, R², R³, R⁴, R⁵, R$^{9a}$, R$^{9b}$, X and Y are as defined in claim 1; or a pharmaceutically acceptable salt thereof.

6. A compound as claimed in claim 1 wherein X represents the NR⁶R⁷ group where R⁶ and R⁷ each independently represent hydrogen, $C_{1-6}$alkyl or $C_{2-4}$alkyl substituted by $C_{1-6}$alkoxy, or R⁶ and R⁷, together with the nitrogen atom to which they are attached, form a saturated heterocyclic ring of 4, 5 or 6 atoms which may optionally contain in the ring one oxygen atom or the group NR⁸, where R⁸ is hydrogen or methyl.

7. A compound as claimed in claim 6 wherein, the group NR⁶R⁷ represents NH₂, NHCH₃, N(CH₃)₂, azetidinyl, morpholino, thiomorpholino, piperazino, piperidino or pyrrolidino.

8. A compound as claimed in claim 1 wherein Y represents a methyl or CH₂OH group.

9. A compound selected from:

2-(R)-(1-(R)-(3,5-bis(trifluoromethyl)phenyl)ethoxy)-3-(S)-(4-fluorophenyl)-4-(4-morpholinobut-2-yn-yl)morpholine;

2-(R)-(1-(R)-(3,5-bis(trifluoromethyl)phenyl)ethoxy)-4-(4-N,N-dimethylaminobut-2-yn-yl)-3-(S)-(4-fluorophenyl)morpholine;

4-(4-azetidinylbut-2-yn-yl)-2-(R)-(1-(R)-(3,5-bis(trifluoromethyl)phenyl) ethoxy)-3-(S)-(4-fluorophenyl)morpholine;

2-(R)-(1-(R)-(3,5-bis(trifluoromethyl)phenyl)ethoxy)-3-(S)-(4-fluorophenyl)-4-(4-imidazolylbut-2-yn-yl)morpholine;

2-(R)-(1-(R)-(3,5-bis(trifluoromethyl)phenyl)ethoxy)-3-(S)-(4-fluorophenyl)-4-(4-(N-methylpiperazinyl)but-2-yn-yl)morpholine;

4-(4-bis(2-methoxyethyl)aminobut-2-yn-yl)-2-(R)-(1-(R)-(3,5-bis(trifluoromethyl)phenyl)ethoxy)-3-(S)-(4-fluorophenyl)morpholine;

2-(R)-(1-(R)-(3,5-bis(trifluoromethyl)phenyl)ethoxy)-3-(S)-(4-fluorophenyl)-4-(4-pyrrolidinobut-2-yn-yl)morpholine;

3-(S)-(4-fluorophenyl)-2-(R)-(1-(R)-(3-fluoro-5-(trifluoromethyl)phenyl) ethoxy)-4-(4-morpholinobut-2-yn-yl)morpholine;

3-(S)-(4-fluorophenyl)-4-(4-morpholinobut-2-yn-yl)-2-(R)-(1-(R)-(3-(trifluoromethyl)phenyl)ethoxy)morpholine;

4-(4-azetidinylbut-2-yn-yl)-3-(S)-(4-fluorophenyl)-2-(R)-(1-(R)-(3-(trifluoromethyl)phenyl)ethoxy)morpholine;

2-(R)-(1-(R)-(3,5-bis(trifluoromethyl)phenyl)ethoxy)-4-(4-(N-(2-methoxyethyl)-N-methyl)aminobut-2-yn-yl)-3-(S)-phenylmorpholine;

2-(R)-(1-(R)-(3,5-bis(trifluoromethyl)phenyl)ethoxy)-4-(4-(N-cyclopropyl-N-(2-methoxyethyl)amino)but-2-yn-yl)-3-(S)-phenylmorpholine;

2-(R)-(1-(R)-(3,5-bis(trifluoromethyl)phenyl)ethoxy)-4-(4-(N-isopropyl-N-(2-methoxyethyl)amino)but-2-yn-yl)-3-(S)-phenylmorpholine;

4-(4-(N,N-dimethylamino)but-2-yn-yl)-3-(S)-(4-fluorophenyl)-2-(R)-(1-(S)-(3-fluoro-5-(trifluoromethyl)phenyl-2-hydroxyethoxy)morpholine;

4-(4-azetidinylbut-2yn-yl)-3-(S)-(4-fluorophenyl)-2-(R)-(1-(S)-(3-fluoro-5-(trifluoromethyl)phenyl)-2-hydroxyethoxy)morpholine;

4-(4-N-bis(2-methoxy)ethyl-N-methylamino)but-2-yn-yl)-2-(R)-(1-(R)-(3,5-bis(trifluoromethyl)phenyl) ethoxy)-3-(S)-(4-fluorophenyl)morpholine;

2-(R)-(1-(R)-(3,5-bis(trifluoromethyl)phenyl)ethoxy)-3-(S)-(4-fluorophenyl)-4-(4-(2-(S)-(methoxymethyl)pyrrolidino)but-2-yn-yl)morpholine;

4-(4-(7-azabicyclo[2.2.1]heptano)but-2-yn-yl)-2-(R)-(1-(R)-(3,5-bis(trifluoromethyl)phenyl)ethoxy)-3-(S)-(4-fluorophenyl)morpholine;

2-(R)-(1-(R)-(3,5-bis(trifluoromethyl)phenyl)ethoxy)-4-(4-diisopropylaminobut-2-yn-yl)-3-(S)-(4-fluorophenyl)morpholine;

2-(R)-(1-(R)-3-fluoro-5-(trifluoromethyl)phenyl)ethoxy)-4-(4-(2-(S)-(methoxymethyl)pyrrolidino)but-2-yn-yl)-3-(S)-phenylmorpholine;

2-(R)-(1-(R)-(3,5-bis(trifluoromethyl)phenyl)ethoxy)-3-(S)-(4-fluorophenyl)-4-(4-(2-(S)-(hydroxymethyl)pyrrolidino)but-2-yn-yl)morpholine;

or a pharmaceutically acceptable salt thereof.

10. The compound:
2-(R)-(1-(S)-(3,5-bis(trifluoromethyl)phenyl)-2-hydroxyethoxy)-4-(4-(N,N-dimethylamino)but-2-yn-yl)-3-(S)-(4-fluorophenyl)morpholine;
or a physiologically acceptable salt thereof.

11. The compound:
4-(4-azetidinylbut-2-yn-yl)-2-(R)-(1-(S)-(3,5-bis(trifluoromethyl)phenyl)-2-hydroxyethoxy)-3-(S)-(4-fluorophenyl)morpholine;
or a physiologically acceptable salt thereof.

12. A pharmaceutical composition comprising a compound as claimed in claim 1 in association with a pharmaceutically acceptable carrier or excipient.

13. A method for the treatment or prevention of physiological disorders associated with an excess of tachykinins, which method comprises administration to a patient in need thereof of a tachykinin reducing amount of a compound according to claim 1, or a pharmaceutically acceptable salt thereof.

14. A method according to claim 13 for the treatment or prevention of pain or inflammation.

15. A method according to claim 13 for the treatment or prevention of migraine.

16. A method according to claim 13 for the treatment or prevention of emesis.

17. A process for the preparation of a compound of claim 1, which comprises:

(A) reacting a compound of formula (II):

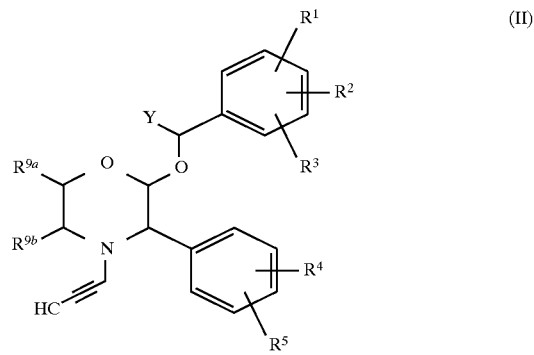

wherein $R^1$, $R^2$, $R^3$, $R^4$, $R^5$, $R^{9a}$, $R^{9b}$ and Y are as defined in claim 1 with formaldehyde followed by the desired amine of formula $HNR^6R^7$, in the presence of a suitable catalyst; or (B) reacting a compound of formula (III):

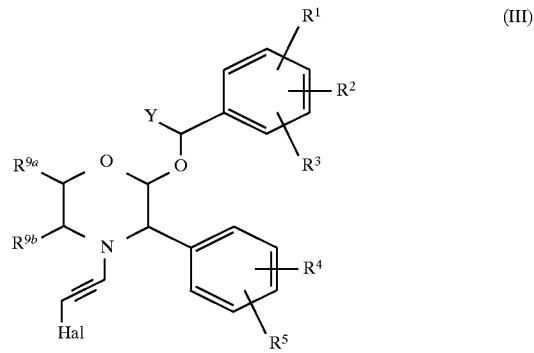

wherein $R^1$, $R^2$, $R^3$, $R^4$, $R^5$, $R^{9a}$, $R^{9b}$ and Y are as defined in claim 1 and Hal is a halogen atom, by reaction with an amine of formula $HNR^6R^7$ or imidazole, in the presence of a base; or (C) the interconversion of a compound of formula (IV):

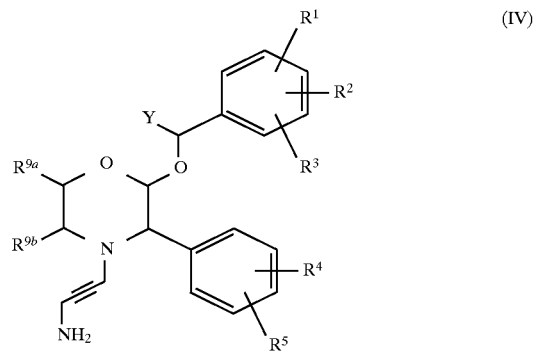

using alkyl halides of the formula $R^6$-Hal and $R^7$-Hal, or a suitable dihalide designed to form a saturated heterocyclic ring, wherein $R^6$ and $R^7$ are as defined in claim 1, and Hal represents a halogen atom, in the presence of a base;

each process being followed, where necessary, by the removal of any protecting group where present;

and when the compound of formula (I) is obtained as a mixture of enantiomers or diastereoisomers, optionally resolving the mixture to obtain the desired enantiomer; and/or, if desired, converting the resulting compound of formula (I) or a salt thereof, into a pharmaceutically acceptable salt thereof.

* * * * *